(12) United States Patent
Spiegel

(10) Patent No.: US 7,288,062 B2
(45) Date of Patent: Oct. 30, 2007

(54) APPARATUS FOR CREATING THERAPEUTIC CHARGE TRANSFER IN TISSUE

(76) Inventor: Michael Spiegel, 199 Palm Ave., Miami Beach, FL (US) 33139

( * ) Notice: Subject to any disclaimer, the term of this patent is extended or adjusted under 35 U.S.C. 154(b) by 477 days.

(21) Appl. No.: 10/801,168

(22) Filed: Mar. 12, 2004

(65) Prior Publication Data

US 2005/0065394 A1    Mar. 24, 2005

Related U.S. Application Data

(63) Continuation-in-part of application No. 10/035,854, filed on Nov. 9, 2001, now abandoned.

(51) Int. Cl.
*A61N 2/02* (2006.01)
(52) U.S. Cl. .......................................................... 600/9
(58) Field of Classification Search .............. 600/9–15; 607/2, 65
See application file for complete search history.

(56) References Cited

U.S. PATENT DOCUMENTS

| | | | |
|---|---|---|---|
| 2,939,976 A * | 6/1960 | Manni .......................... 310/196 |
| 3,051,988 A | 9/1962 | Baermann |
| 4,105,017 A | 8/1978 | Ryaby et al. |
| 4,266,532 A | 5/1981 | Ryaby et al. |
| 4,266,533 A | 5/1981 | Ryaby et al. |
| 4,315,503 A | 2/1982 | Ryaby et al. |
| 4,727,857 A | 3/1988 | Hörl |
| 5,200,071 A | 4/1993 | Spiegel |
| 5,224,922 A * | 7/1993 | Kurtz ............................ 600/13 |
| 5,314,400 A * | 5/1994 | Tsyb et al. ...................... 600/9 |
| 5,338,286 A | 8/1994 | Abbott et al. |
| 5,544,665 A * | 8/1996 | Litovitz et al. .............. 128/897 |
| 5,968,527 A * | 10/1999 | Litovitz ....................... 424/400 |
| 5,983,134 A | 11/1999 | Ostrow |

(Continued)

OTHER PUBLICATIONS

A.I. Ivashina et al.: "Magnetic Field Therapy to Support Keratotomy", *Cataract Surgery*, vol. 4, 1991, pp. 37-40.
Richard B. Borgens et al.: "Effects of applied electric fields on clinical cases of complete paraplegia in dogs", *Restorative Neurology and Neuroscience*, vol. 5, 1993, pp. 305-322.

*Primary Examiner*—Charles A. Marmor, II
*Assistant Examiner*—Christine Hopkins
(74) *Attorney, Agent, or Firm*—Loren D. Pearson; Paul D. Bianco; Fleit Kain Gibbons Gutman Bongini & Bianco P.L.

(57) ABSTRACT

An apparatus for creating therapeutic charge transfer in tissue includes a coil. The coil generates a changing magnetic field to induct an electric field in the tissue exceeding 10 mV/cm when the coil is 5 cm from the tissue. Preferably, the magnetic field has a growth phase and a decay phase and a duration of the growth phase is at least ten times a duration of the decay phase. The apparatus can include a control circuit to control a current fed to the coil. The control circuit includes two subcircuits and a switch for switching between a first of the subcircuits and a second of the subcircuits; preferably, a λ of the second subcircuit is at least ten times a λ of the first subcircuit. To generate the therapeutic effect, the coil should have a duty cycle of at least ten percent.

26 Claims, 13 Drawing Sheets

U.S. PATENT DOCUMENTS

| | | |
|---|---|---|
| 6,086,572 A | 7/2000 | Johnson et al. |
| 6,561,968 B1 * | 5/2003 | Dissing et al. ................ 600/13 |
| 6,589,786 B1 * | 7/2003 | Mangano et al. ........... 435/372 |
| 7,088,210 B2 * | 8/2006 | Day et al. ..................... 336/60 |
| 2002/0169355 A1 | 11/2002 | Rohan et al. |
| 2003/0171640 A1 * | 9/2003 | Canedo ......................... 600/9 |

* cited by examiner

APPARATUS FOR CREATING THERAPEUTIC CHARGE TRANSFER IN TISSUE

CROSS-REFERENCE TO RELATED APPLICATION

This application is a Continuation-In-Part of U.S. application Ser. No. 10/035,854, filed Nov. 9, 2001 now abandoned.

BACKGROUND OF THE INVENTION

1. Field of the Invention

This invention relates to applying electric fields to various parts of the body for medical treatment. More specifically, this invention applies a changing magnetic field on human tissue, wherein the time change of magnetic field strength (dB/dt) produces a resultant electromotive force (EMF) on the ions in the tissue such as that caused by a direct electric current between two electrodes. Thus, the invention treats human tissues with time changing magnetic fields that induce an electric field.

The invention also lies generally in the field of ion propulsion. More specifically, the invention relates to using a moving magnetic field such as those found in the area of plasma physics with certain applications concerned with rocket propulsion and controlled fusion. The application of this invention is not in these areas but is in a lower energy regime with application for the medicinal treatment of human bone, blood, tissue, and organs by the application of an electric field without the use of electrodes.

2. Description of the Prior Art

DC-like currents are recognized as providing medicinal benefits when applied to biological materials. For example, DC-like currents applied on or beneath the skin's surface have been effective in promoting rapid healing of bones, tissues, and even regrowth of spinal cord axons.

Typical apparatus have relied on electrode-imposed electric fields to impart the electromotive force required to produce the DC-like electric currents in treated tissues. The electrodes are inserted beneath the skin. For example, the use of electrodes to induce currents to treat spinal cord injuries is disclosed in Borgens et al., "Applied Electric Fields in Clinical Cases of Complete Paraplegia in Dogs." *Restorative Neurology and Neuroscience*, Vol. 5, pp. 305-322 (1993).

The invasive nature of electrodes threatens the beneficial outcome of the clinical treatment and production of uniform electric fields within the treated tissue. For example, the electrodes can cause infection or become displaced. Moreover, the electric fields produced are non-uniform in both intensity and geometry due to the polarization of the surrounding media at each electrode with oppositely charged ions that weaken and distort the electric field.

The basic concept for the beneficial application of a magnetically generated Lorentz force field to a volume is disclosed in Spiegel (U.S. Pat. No. 5,200,071). In contrast, the invention of the instant application discloses an invention that generates an equivalent electric field with both dynamic and time changing magnetic fields. The invention of the instant application further discloses an invention that generates an equivalent electric field that will stimulate the growth, repair, and renewal of damaged human bone, blood, tissue, and organs. The equivalent electric field also can be used to block specific nerve signals to eliminate pain. The equivalent electric field allows the transdermal transport of efficacious ionic components to specific locations within the tissue. The equivalent electric field can be increased to such power that it will destroy certain volumes of cancerous tissue.

Baermann et al. (U.S. Pat. No. 3,051,988) disclose a magnetic material manipulation device that is superficially similar in appearance to an embodiment of the device disclosed herein. Baermann's device is intended to handle magnetic material for industrial purposes. It uses low rotational velocities and does not generate significant electrical fields. It has no specified medical application and has no mention or understanding of the field generation process disclosed herein.

In a series of patents, Ryaby et al. (U.S. Pat. No. 4,105,017; U.S. Pat. No. 4,266,532; U.S. Pat. No. 4,266,533; and U.S. Pat. No. 4,315,503) disclose a magnetically induced current of specific frequency and amplitude for clinically treating living tissue. The current is induced by an electromagnetic coil. As the coil is electrically energized, it generates a resultant time varying magnetic field. The electric field, and consequent electric current induced by such a coil, must be of a reversing nature. The system disclosed could never produce a DC or rectified AC electric current in treated tissue. Instead, Ryaby et al. produce pulses of induced AC current of specific frequencies and modulations that, although contradicting the teachings of the other references, are purported to be clinically efficacious.

Furthermore, Ryaby et al. teach a medical treatment device that is capable of generating only AC current. The AC current is developed by a time varying single electromagnetic coil that is spatially static. Ryaby et al. in no way suggest the development of electric currents from spatially dynamic magnetic fields. Ryaby et al. do not suggest the generation of electric fields with a stepwise changing magnetic field.

Horl (U.S. Pat. No. 4,727,857) discloses a moving disk with a single set of opposite polarity permanent magnets on one or both faces of the disk. This device produces spatially dynamic magnetic fields that will generate a reversing sinusoidal electric field with each revolution of the disk. Horl teaches to produce only purely sinusoidal electric fields and currents near the surface of each magnetic pole face. Therefore, Horl neither teaches nor suggests to use asymmetrical directed electric currents are an intended resultant clinical benefit. Rather, Horl merely teaches to provide such clinical benefit as may accrue through the action of a pulsing magnetic field of a singular geometry. Such electric fields as generated by this device will be sinusoidal and thus, as shown by cited studies (i.e. Reich and Tarjan) of little therapeutic benefit.

In the article titled "Magnetic Field Therapy to Support Keratotomy," Ivashina et al. teach to use a moving set of magnets to enhance recovery rates and reduce pain. Ivashina teaches to generate a field that is purely sinusoidal and as a result produces very limited charge transport. Ivashina et al. do not teach or suggest a "square wave" electric field that can produce significant charge transport of the type required by the DC-like current shown to be effective in the Reich & Tarjan study. In addition, Ivashina et al. teach to use simple split fields and not a continuous exposure to a magnetic array. In addition, Ivashina et al. do not teach or suggest incorporating specifically designed permanent or electromagnets that generate dynamic and stepwise changing magnetic fields to induce a continuous and uniform DC-like "square wave" electric field.

Although Abbott et al. (U.S. Pat. No. 5,338,286) do show a magnetic field that increases at a constant rate over 230

μsec and then decreases rapidly over 30 μsec (i.e. FIG. 1), the device taught would be incapable of working at the higher voltages and currents necessary to heal tissue in the same manner that a direct current made between electrodes would.

The issue as to the rejection as being anticipated by Abbott et al. is weather on not someone skilled in the art would be able to extend the inefficient application that Abbott et al. teaches by at least two orders of magnitude to the present teaching.

Furthermore, Abbott et al. focus on producing a rounded saw-tooth shaped magnetic field. Abbott et al. stated the following in col. 2, lines 26-35:

> We have discovered that the known biological and therapeutic stimulation by pulsing magnetic fields or by pulsing induced or direct electric fields as practiced with the application of pulses which have heretofore been configured with rapid changes in magnitude or direction of the fields can be improved significantly by modifying the configuration of these pulses to selectively reduce the higher-frequency components of the equivalent spectrum. (Emphasis added by Applicant.)

Therefore, the object of Abbott et al. is to modify only the leading edge of the longer positive pulse. In addition, Abbott et al. state at col. 4, lines 3-7, the following:

> It has been found that the bioresponse of PEMF signals is sharply improved when the rise and fall times in the electric field are lengthened, and, in particular, when the amplitude changes are made less abrupt by rounding the profile of the pulses."

While other earlier teachings, i.e. Ryaby etc., focus on the distinction of variable rates of increase and decrease in the magnetic and thus the induced electric fields, the Abbott et al. merely suggest producing "bursts" of asymmetrical signals. None call for continuous repetitive asymmetrical signals without a delay between repetitions. In contrast, Abbott et al. Claim pulse trains of approximately one hundred (~100) cycles at a frequency of approximately 40 kHz. These 40 kHz bursts are repeated at a frequency of 1.5 Hz or every 0.667 seconds. Thus, during every two-second interval of "treatment", the sum total time for the three one-hundred cycle bursts would be 0.075 seconds. However, while this percentage may vary slightly within the prior art, it remains representative.

Although Abbott et al. make no direct reference to the actual strength of the induced electric fields in the treated tissue, Abbott et al. cross-reference Ryaby. Ryaby (U.S. Pat. No. 4,105,017) teaches a pattern of pulses similar to that of Abbott et al. Because the direction of the signal (i.e. positive or negative) is arbitrary and subject to sensor orientation, the overall shape of the signal is determinant. As discussed in detail below, there are two portions during each cycle of the induced electric field. Any asymmetric electric field that is generated by a pulsed magnetic coil will have a larger voltage for the faster (shorter in time) part of the cycle and a lower voltage for the longer lasting part of the cycle. Thus, in Ryaby, the "positive" portion of the cycle is similar to the negative portions of Abbott et al.; the same is true of Ryaby's negative going voltage. With regard to the longer lasting part of the cycle, Ryaby claims a maximum of 3.7 mV/cm (0.0037 volts/centimeter) "at the face of the treatment coil" and 1 mV/cm at a distance of ~3.8 cm "from the face of the treatment coil".

Abbott et al. and Ryaby teach waveforms that yield a very specific therapeutic effect on bone. The results being claimed by them result from a variety of short pulse trains of electric field at high frequency.

In contrast to Abbott et al. and Ryaby, the medical community as proffered by Reich et al. in *The International Journal of Dermatology* is that the primary determinative factor in therapeutic benefit of applied electric fields is the effective transport of a minimum quantity of electric charge. That is, there is a measurable therapeutic result only if a specific amount of electric charge is moved in the volume of the wound. Although claims of therapeutic results are made for various adaptations of the existing technology, all creditable claims in the prior art refer to bone treatment with days and weeks of nearly continuous treatment. Because bones have a much higher conductivity than other tissues, it is possible with extended treatment times to produce the required transfer of charge.

The remaining prior art has attempted to treat the above clinical problems with the insertion of electrodes to generate an electric field. The breath and effectiveness of these methods are described in the following publications: "Electric Fields in Vertebrate Repair" and "The Body Electric". Evidence of the potential application to regeneration of nerve tissue in mammals is most recently given by Borgens et al. in the report, "Applied electric fields . . . in Dogs." All of these references agree that the most significant beneficial results are obtained through the application of DC currents that mimic the body's own mechanism.

Ryaby (U.S. Pat. No. 4,315,503) rely on physical assumptions that as described are either unclear or incorrect. Furthermore, Abbott et al. encorporate by reference Ryaby. Both patents by Ryaby (U.S. Pat. Nos. 4,315,503 and 4,105,017) teach a circuit as follows:

> The signal across the treatment coil decays in a second pulse segment along the portion of the curve designated 40 in FIG. 5*a*. The slope of that curve is determined by the L/R time constant of the circuit of FIG. 4, i.e., the inductance of the treatment coil and the effective resistance of the circuit, including distributed factors of capacitance, inductance and resistance.

Clearly there is no teaching of a second circuit with a different value for L/R. In addition, Ryaby states, "In FIG. 5*a*, the signals at the treatment coil 22 and hence the induced signal within the tissue to be treated are shown." In general, this is not a true statement. The voltage or "signal" induced within the tissue will not be identical or the "same" as the voltage at the coil. It is established that the induced signal is a function of the time rate of change of the magnetic field within the tissue, dB/dt. The magnetic field is a direct function of the current, i(t), within the coil and as is shown in the current patent:

$i = i_0 \{1 - e^{-(R/L)t}\}$ for the growth of current in the coil,
and $i = i_0 e^{-(R/L)t}$ for the decay of current in the coil.

The exception to this would be for very short times, t, when t>>L/R. Under this exception, the voltage signal imposed on the coil will induce a smaller but similar signal in the tissue.

If the signal being imposed on the coil is repetitive, then:

$i \approx E/2\pi f$ if $2\pi fL >> R$ where f is the frequency of the cycle, L the inductance of the coil, and R the total resistance in the circuit. Thus, at very high frequencies, the response of the current in the coil is nearly instantaneous with minimal growth and decay times between imposing a voltage on the coil and having full current in the coil.

This assumption is contradicted by Ryaby in claim 1(*c*) of U.S. Pat. No. 4,105,017 where he claims burst pulse frequencies of between 500 Hz and 100 Hz. At these low frequencies, the lag time of current growth and decay would be very significant and the above assumptions fail.

Therefore, although Ryaby seems on first glance to be dealing with PEMP, the technology is not cable of inducting the therapeutic currents that are similar to a direct current supplied to tissue directly with electrodes. Certain substantial criteria can only be achieved with a higher energy dual circuit of the type taught by the current patent application.

Likewise, Abbott et al. is not capable of inducing sufficient electric fields with sufficient Duty Cycle to create the therapeutic effects that are similar when connecting a direct current directly to tissue using electrodes.

There is no prior art that teaches a method for achieving strong enough induced electric fields of sufficient duration (Duty Cycle) to produce the necessary quantity of charge transport in tissue of low conductivity.

Abbott et al. do not teach a magnetic field with sufficient Duty Cycle or strength to create therapeutic results. Low energy electric signal wave trains of high frequency bursts, such as those taught by Abbott et al. with long intervals between bursts, produce low energy electric treatment fields with low efficiency Duty Cycles. The Duty Cycle taught by Abbott et al. is a pulse train of approximately one hundred (~100) pulses with a primary signal of two hundred microseconds (200 µs) and an opposite polarity signal of fifty microseconds (50 µs), to be repeated at 1.5 Hz frequency or a period of 0.667 s.

The following formula calculates this Duty Cycle:

$$D.C.=((0.0002*100)/0.667)*100=3\%$$

Thus, the effect of the primary signal is transmitted to the patient for 3% of the time of the treatment. The electric field strength of Abbott et al.'s teaching is not directly disclosed. Abbott et al. state that the coil that produces his induced electric field is powered by a 1 volt regulated DC power supply. Simple analysis of the inductance and driving voltage yields maximum electric treatment field strength of less than fifty 0.5 microvolts per centimeter (<0.5 µV/cm). Voltages in this range will yield nanoamps (0.000000001 A) or less induced in the patient. However, Reich et al. have established that currents in the microamp (0.000001 amps) range are required for effective therapeutic results. If higher induced voltages are achieved, as claimed, they are of such short duration and of such low Duty Cycle efficiencies (3-7%) as to make charge transport negligible.

The teachings of Abbott et al., Ostrow, Rohan, and Ryaby are capable of producing effective electric fields that are two or three orders of magnitude less than the current invention. The methods used by the earlier teachings will not allow for the currents, voltages, or Duty Cycles that are necessary to produce sufficient electric charge transport as defined by Reich et al.

As has been shown above and in the current patent application, such levels of energy transmission and Duty Cycles can only be produced by at least a two order of magnitude enhancement of any of the prior art. Any increase of such magnitude requires a significantly change in the overall design and circuits.

The extension of previous teachings by someone skilled in the art will not resolve the problems of low Duty Cycle or deal with the high volt discharge and high temperature concerns that are created with the significantly higher power of the current invention.

Rohan teaches a symmetric magnetic field waveform. As a result, no net charge transport is produced. Accordingly, no therapeutic effects would result in the treated tissue. Using the model of the current teaching the Duty Cycle for Rohan is 0% since a purely sinusoidal has equal positive and negative going portions and thus will do no work in transport of charges.

Furthermore, the teachings of Rohan et al. do not suggest the invention of the instant application. If we assume, as may be the case in bone, that there is a rectifying effect and only one part of the sine wave is effective and the other half is blocked (half wave rectified). To start with Rohan and then eliminate the delay between pulse trains as is suggested by Rohan at the bottom of the cited paragraph, the Duty Cycle equals 43% using only the "plateau" of the trapezoidal pulse. This is better than 7% of Abbott et al. but less than one half of the 88% of the current teaching. This technology and circuit design would never lead to an effective charge transport system in tissue.

Ostrow does teach a system that is functional description of a delivery system for electrophoresis, if an effective signal that will transport the ions can be generated. Ostrow only teaches a sinusoidal and trapezoidal waveform. As previously shown, such a shape will not have a charge transport capability.

Even a combination of Abbott et al. and Ostrow will yield a minimal benefit. Effective use of Ostrow's teaching will require waveforms of higher power and Duty Cycle.

Abbott et al. refer to Ryaby Pat. No. 4,315,503 as being, "hereby incorporated by reference along with the entirety of said patent." Since this specific inclusion of description is made the use of that description may be used unless it is specifically delineated against within the Abbot patent. Certain aspects of the Ryaby patents rely on physical assumptions that as described are either unclear or incorrect.

Ryaby, in both U.S. Pat. Nos. 4,315,503 and 4,105,017, describe a circuit having the following features:

"The signal across the treatment coil decays in a second pulse segment along the portion of the curve designated 40 in FIG. 5a. The slope of that curve is determined by the L/R time constant of the circuit of FIG. 4, i.e., the inductance of the treatment coil and the effective resistance of the circuit, including distributed factors of capacitance, inductance and resistance."

Clearly there is no teaching of a second circuit with a different value for L/R.

SUMMARY OF THE INVENTION

It is accordingly an object of the invention to provide an apparatus for creating therapeutic charge transfer in tissue, which overcome the above-mentioned disadvantages of the heretofore-known devices and methods of this general type.

With the foregoing and other objects in view there is provided, in accordance with the invention, an apparatus that produces a DC-like electric field within biological material, such as living cells and tissue, to obtain a desired clinical benefit without the use of invasive electrodes. This generated electric current mimics the natural mechanism of the cells of tissue. In addition, the present invention avoids the side effects associated with electrodes, such as infection and unwanted mineral deposits.

With the foregoing and other objects in view there is provided, in accordance with the invention, an apparatus for treating biological material. The apparatus includes at least two magnets and a drive. The magnets each produce a magnetic field that combines to form a magnetic field on the biological material. The drive is for changing the magnetic field on the biological material.

In accordance with a further object of the invention, a method for inducing a DC-like electric field in biological tissue includes the following steps. The first step is increasing a magnetic field on the biological tissue. The next step is suddenly decreasing the magnetic field. The method can then be cyclically repeated to create a magnetic field having a saw-tooth shaped intensity over time.

An asymmetric waveform is a necessary component to achieve any degree of charge transport.

Generating beneficial and curative DC-like electric fields by moving and stepwise changing magnetic fields allows the treatment of patients without resorting to the dangerous invasive techniques required by direct application of equivalent electric fields.

To be therapeutic, the electric field being used must be sufficiently strong. While the prior art teaches DC-like electric fields by continuously changing an asymmetrical magnetic field, the invention applies a different mechanism for treating patients without resorting to dangerous invasive techniques required by direct application of equivalent electric fields. The prior art has not provided circuitry that will support electric fields of the required strength or length of exposure to achieve a therapeutic result in tissue. Reich and Tarjan have shown that significant electric charge transport is required to produce a therapeutic effect.

A soon to be published paper by the Department of Dermatology & Cutaneous Surgery at the University of Miami Medical School will describe the results of burn wound treatment with a prototype of the current teaching. The results were dramatic as the wounds healed (as defined by a classic protocol) on average three days faster than untreated wounds on the opposite side of the same animal. The total treatment time was one and one half hour per day for five days post wounding. This is a total treatment time of seven and one half hours. Contrast this with the often hundreds of hours required by prior art. The parameters of interest on this apparatus are a Duty Cycle of 88% and an induced voltage for the longer lasting (DC like) part of the cycle of 25 mV/cm (0.025 V/cm) at a separation from the coil face of five centimeters (5 cm).

Improved "Duty Cycle" is a key feature of the invention. As defined by the independent study cited, an active portion of a treatment cycle is that portion that has the longer lasting part (i.e. the long increasing magnetic field compared to the overall period of the waveform). It is possible to compute the commonly used percentage to designate the effective rate at which any system is being used. This quantity is called the Duty Cycle and is defined by the active time of the cycle divided by the total time of the cycle multiplied by 100 to give a percentage: Duty Cycle={(time on)/(time on+time off)}×100. Using this criteria, the apparatus according to the invention is capable of a Duty Cycle in excess of 90%. As noted, a typical setting is 88%. The maximum Duty Cycle claimed by any of the prior art is 7% with a typical setting of 3 to 4%.

Two distinctions between the invention of the instant application and the prior art are the Duty Cycle and the effective electric field in the treated tissue. The ability to produce charge transport is a direct function of EMF (Electro Motive Force or applied voltage) multiplied by the total time of exposure to that force. Although other factors such as conductivity play an important role, the primary determinants are force over time. Thus, the Duty Cycle multiplied by the voltage per unit length (V/cm) at the treatment site will give a reasonable comparison of effectiveness.

Using Ryaby's claim of 2.5 mV/cm at a distance of ~1.6 cm "from the face of the treatment coil" and choosing a maximum of 7% Duty cycle (an alternative is the total on time/second of treatment, i.e. 0.07 seconds in this case) and the EMF of forty millivolts per centimeter (40 mV/cm) for the current teaching's prototype at ~2.0 cm from the face of the coil and a Duty Cycle of 88% we get:

Effectiveness Coefficient (prior art)=2.5×7=17.5
Effectiveness Coefficient (current teaching)=40× 88=3520

This is a ratio of just over 200 to 1.

This does not take into account the probable loss of effective transmission of energy due to the relatively short exposure at the higher frequency of prior art. Effective electric charge transport is primarily produced during the "DC" like portion of the Duty Cycle. During this time, $\Delta t_G$, a nearly constant Electro Motive Force (EMF) is imposed on all charges in the tissue within the electric field. In order to be effective in producing actual sustained transport the charges must be moved a distance significantly greater than a few Debye Lengths. In the low conductivity of tissue, the short duration of the reverse EMF during the time $\Delta t_D$ has a reduced effect in achieving transport greater than a single Debye Length." A typical $\Delta t_G$ for the current apparatus is 0.008 seconds and a typical $\Delta t_G$ for prior art such as Abbott et al. is 0.00023 seconds. Although actual measurement of the minimum time and the EMF necessary to achieve charge transport have not been measured definitively in tissue, it is clear that a minimum exists, below which there will be no beneficial result (see Reich et al.).

The prior art is not able to produce therapeutic effects in tissue because the magnetic fields produced do not employ sufficient amperage to induce a signal of the necessary energy or duration. The power used by the prior art has been of such low intensity as not to require specific cooling of either the treatment coil or electronics. This is significant in that the transmission of strong and high Duty Cycle electric fields inductively requires high amperage. The dissipation of the energy stored in the electric and magnetic fields of the coil also produce both high currents and voltages in excess of two kilovolts (2 kV, 2000 V). High currents generate heat. The typical "high temperature" of prior-art coils is 40° C. using only radiation of heat to cool. No mention is made of cooling the resistors used in the circuits of prior art. Although much larger currents and induced voltages are possible with the current teaching all, including the current prototype, require significant cooling systems.

The temperature of the coil in the current prototype is stabilized at 130° C. by the continuous flow of 7-9° C. water through the interior of the coil. The ballast resistors that absorb the energy stored in the coil exceed 300° C. without cooling and can be stabilized at ~230° C. with forced air-cooling.

The foregoing is indicative of the large differences between prior art and the current teaching. These differences of scale require very different and novel methods of controlling all the diverse parameters that are the normal part of electric coil design. Added to the standard problems are the absolute necessity of dealing with very large voltage spikes and high current flows as the two circuits of the coil are turned on and off. The high Duty Cycle means that currents are constantly flowing in or out of the coil. There is no OFF time as in the prior art where coils are energized less than 7% of the time. The attempt to extend the prior art in a conventional way (i.e. using someone skilled in the art) will lead to many destructive events in the circuits as taught. None of the circuits as taught will translate into this higher energy regime. For example, simply adding transistors with a higher standoff voltage will not suffice. Without understanding that the goal of any new design is to produce maximum charge transport and that such a goal will require much higher currents and Duty Cycles no one skilled in the art would attempt to solve the myriad very difficult problems posed by a minimum of two orders of magnitude increase in signal efficiency. All prior art has been based on high frequency low Duty Cycle systems that presuppose a beneficial therapeutic effect without a direct causal theory. Current teaching has solved the problems and can provide as much as three or four orders of magnitude ($10^3$ or $10^4$) increase in charge transport efficiency.

In accordance with a further object of the invention, a duty cycle with an efficiency greater than 10% yields therapeutic results. In addition, the generation of induced spatial electric fields greater than 10 mV/cm is needed for the effective transport of sufficient quantities of electric charge within the tissues to produce the desired therapeutic result.

In accordance with a further object of the invention, a method to create an electric field that is both powerful and effective is disclosed herein. When an electromagnet is charged by an external power source such as a battery, it must obey certain physical laws pertaining to the transfer of energy within such a system. The magnitude of the magnetic field of the electromagnetic could depend on the amount of current, i, flowing through the coil. This current, i, does not rise to its maximum value, $i_0$, instantaneously, but rather is a time dependent function of the coil's inductance, L, and resistance, R. The governing equation for the rise of current and thus the magnetic field of the coil is:

$$i = i_0 \{1 - e^{-(R/L)t}\}$$

Where $i_0$ is the maximum value that the current, i, can reach. The ratio L/R is called the time constant, $\lambda$. The decay of the current when the power source is disconnected after a time $t >> \lambda$ is:

$$i = i_0 \{e^{-(R/L)t}\}$$

Typical growth and decay curves of the current and magnetic field versus time for a coil are shown in FIG. 16. In the case of the growth portion of the chart ($\Delta t_G$), a time constant where $R \approx L$ ($\lambda - 1$) shows a current and resultant magnetic field that has a slow asymptotic approach to maximum. In the decay portion of the chart ($\Delta t_D$), an $R \approx 10L$ produces a very rapid decline in the current and magnetic field produced by the coil. As is well known, the electric field induced by the exposure to a time changing magnetic field is proportional to dB/dt. In order to produce a nearly constant electric field in excess of 10 mV/cm and, with a very short reversal such as shown in FIG. 15A, it is necessary to set up two circuits. The first circuit shown in FIG. 13A allows the initial constant growth rate of the magnetic field that produces a flat DC-like electric field. In order to achieve the rapid reversals of field and then begin again the charge cycle of the coil, it is necessary to have a rapid decay of the energy stored in the coil. This rapid decay of magnetic field and coil energy is achieved by the very fast switching of the coil into a second circuit (FIG. 13B) containing a very large resistance.

In order to achieve the resultant induced electric field shown in FIG. 15A, it is necessary to have a method of switching circuits that will allow the asymptotic growth of the B field with $\lambda \leq 1$ and then switch in a very fast way to a circuit with $\lambda \geq 10$, which will produce the rapid decay of the B field as shown in FIG. 15B. In order to produce an effective resultant frequency, the total time for the growth phase of the cycle, $\Delta tG$, must be approximately ten times the decay phase, $\Delta tD$. Thus, for optimum effect of the resultant E field, the following condition must be met: $\Delta t_G \geq 10 \Delta t_D$.

"Duty Cycle" is the term used to define the total percent of the entire time of a treatment in which the subject is exposed to the effective or beneficial electric field. Within the context of the invention, a possible duty cycle should have a positive DC-like portion of the electric field for 0.008 seconds and a negative portion for 0.002 seconds that continuously repeats, without any time interval between cycles. For this example, the Duty Cycle (DC) is:

$$DC = ((0.008/(0.008+0.002))*100 = 80\%$$

Although the frequency in this example is 1000 Hz, it may be useful to use both higher and lower frequencies and or Duty Cycles.

Reich et al. have proven by a broad analysis of numerous electrical stimulation experiments that the fundamental characteristic of a beneficial therapeutic outcome is the electric field that must produce an absolute charge density transfer of approximately 0.1-2.0 $C/cm^2$.

Reich et al. in the *International Journal of Dermatology* validate this conclusion with the results compiled from seventeen different medical studies. Further validation of the efficacy of charge transfer is provided by the experiments using the inventor's device at the University of Miami's Medical School where definitive results were achieved in healing burn wounds.

Effective electric charge transport is primarily produced during the "DC" like portion of the Duty Cycle. During this time, $\Delta t_G$, a nearly constant Electro Motive Force (EMF) is imposed on all charges in the tissue within the electric field. In order to be effective in producing actual sustained transport, the charges must be moved a distance significantly greater than a few Debye Lengths. In the low conductivity of tissue, the short duration of the reverse EMF during the time tD has a reduced effect in achieving transport greater than a single Debye Length and thus differential charge transport is achieved by the long duration part of the cycle.

In order to achieve an effective transfer of electric charge, there is a minimum threshold of electric field and effective exposure to that field. Thus, both Duty Cycle and electric field intensity must be large enough to produce the necessary movement of charges during the total period of exposure in order to produce a therapeutic benefit. It will be demonstrated that none of the prior art teaches an effective technology for obtaining this result.

Abbott et al., Ostrow, Rohan, and Ryaby, have all relied on low energy higher frequency pulsed discharges that allow rapid rise and decay times because the energy stored in the inductive coil is minimal and thus can decay at a rate that allows the use of low voltage signal based drive currents. These systems typically employ currents as low as one ampere ($\geq 1$ A) and drive voltages less than five volts (<5V).

In accordance with a further object of the invention, the circuit that will achieve the required parameters is taught herein and detailed in the embodiment detailed below. The circuit has a high percentage Duty Cycle, a powerful induced electric field strength, and high speed switching of circuits. FIG. 12 shows this power circuit. This circuit includes two separate sub circuits that produce the required currents and voltages.

When the control signal 11 is "on" (the longer portion of the square wave), the circuit connects from the positive electrode of the Power Supply to the coil and through the switching IGBT (Insulated Gate Bipolar Transistor) to ground. This is the circuit shown in FIG. 13A. It will then produce a growth rate for the initial current in the circuit with a $\lambda_{ON}=L/R_L$. When the control signal 11 is "off" (the shorter portion of the square wave), it causes the IGBT to momentarily open the circuit to ground. The energy stored in the coil will flow in a closed loop circuit through diode 114 and large resistance $R_P$ 108 as shown in FIG. 13B. No further current will come from the positive electrode of the Power Supply while there is no ground connection. When the ground connection is interrupted, the new circuit has a $\lambda_{OFF}=L/(R_L+R_P)$. Because $R_P>>R_L$, this much smaller $\lambda_{OFF}$ allows for the rapid decay of the current in the circuit. At which time, the IGBT is reconnected to ground and the cycle repeats.

FIG. 3A illustrates the effective circuit when IGBT is connected to ground. It is during this phase of the cycle that the coil is being electrically energized and the time changing magnetic field creates a "DC like" electric field in the space infused by the magnetic field.

FIG. 3B shows the effective circuit when the IGBT is not connected to ground and the energy stored in the coil is dissipated in the large resistance, $R_p$, and the short time reverse electric field is generated by the coil. It should be noted that this circuit is a closed loop and without any ground, although a capacitive connection to ground, called a "snubber" prevents excessively high voltages as the current is dissipated.

This dual circuit system allows the large currents that are required for effective therapy to flow into the treatment coil thereby storing large amounts of energy in the coil. This energy must then be very quickly dissipated to allow an immediate repetition of the cycle. The high-speed removal of the energy from the coil allows for both a high-energy electric treatment field and a high efficiency Duty Cycle. The exchange of energy between the coil and the resistance $R_P$ produces a very large voltage spike in the circuit that can only be withstood by an IGBT or equivalent series of power transistors.

In accordance with a further object of the invention, the invention can withstand the high voltage that is created during the reversal of the electric field in the treatment coil. This voltage spike can exceed two thousand volts (>2000 V).

In accordance with a further object of the invention, the apparatus according to the invention can incorporate a liquid cooling system to prevent failure of the coil due to high temperatures created by the large currents in the coil.

Additional features and advantages of the invention will be set forth in the description which follows, and in part will be apparent from the description, and may be learned by the practice of the invention. The objects and advantages of the invention will be realized and attained by the device particularly pointed out in the written description and claims hereof as well as the appended drawings.

To achieve these and other advantages and in accordance with the purpose of the invention, as embodied and broadly described, the invention provides an apparatus of either permanent magnets or electromagnets arranged and prepared so as to cause the stepwise changing of arranged or generated magnetic fields relative to the tissue in which the desired DC-like electric filed is to be induced. The stepwise changing of such magnetic fields by the apparatus induces a force on electrons within living cells and tissue and generates a DC-like electric current in the cells or tissue.

In accordance with a further object of the invention, the invention may include an apparatus for the treatment where the magnets are permanent magnetic material with coercivity greater than 1 kOe.

In accordance with a further object of the invention, the apparatus can include a plurality of electromagnets.

In accordance with a further object of the invention, the apparatus can include at least one driven disk-like member with an outer peripheral surface where discrete stepwise changing permanent magnets form the magnetic material on the surface.

In accordance with a further object of the invention, the invention may include an apparatus for the treatment including at least one driven disk-like member with a groove on its outer peripheral surface, wherein a plurality of discrete stepwise changing electromagnets form the magnetic material.

In accordance with a further object of the invention, the invention may include an apparatus for the treatment including at least one driven disk-like member with an outer peripheral surface, where magnetic material of discrete stepwise changing permanent magnets is on the surface of the groove.

In accordance with a further object of the invention, the invention may include an apparatus for the treatment including at least one driven disk-like member with a groove on its outer peripheral surface, where a plurality of electromagnets form the magnetic material of discrete stepwise changing magnets on the surface of the groove.

In accordance with a further object of the invention, the invention may include an apparatus for treatment including a series of sequentially wound electromagnets fitted closely together and sequentially energized so as to create a uniformly stepwise increasing induced magnetic field with a maximum coercivity greater than 1 kOe and a frequency no less than 30 Hz.

In accordance with a further object of the invention, the invention may include an apparatus for treatment including a sequential array of electromagnets. A magnetic control device is disposed to sequentially apply a pulse of electric current to each electromagnet in the array in order to generate a moving magnetic field that changes in a stepwise fashion with each shift of the field along the array.

In accordance with a further object of the invention, the invention may include an apparatus for treatment including a toroidal sequential array of electromagnets. A magnetic control device disposed to sequentially apply a pulse of electric current to each electromagnet in the array in order to generate a moving magnetic field that changes in a stepwise fashion with each shift of the field along the array.

In accordance with a further object of the invention, frequencies from 1 Hz to 5000 Hz have been found to be therapeutic. However, some applications may require even higher or lower frequencies.

It is to be understood that both the foregoing general description and the following detailed description are exemplary only and are not restrictive of the invention, as claimed.

The accompanying drawings, which are incorporated in and constitute a part of this specification, illustrate several embodiments of the invention and together with the description serve to explain the principles of the invention.

BRIEF DESCRIPTION OF THE DRAWINGS

FIG. 8 was duplicative of FIG. 6 and has been canceled;

DESCRIPTION OF THE PREFERRED EMBODIMENTS

Figure 2:
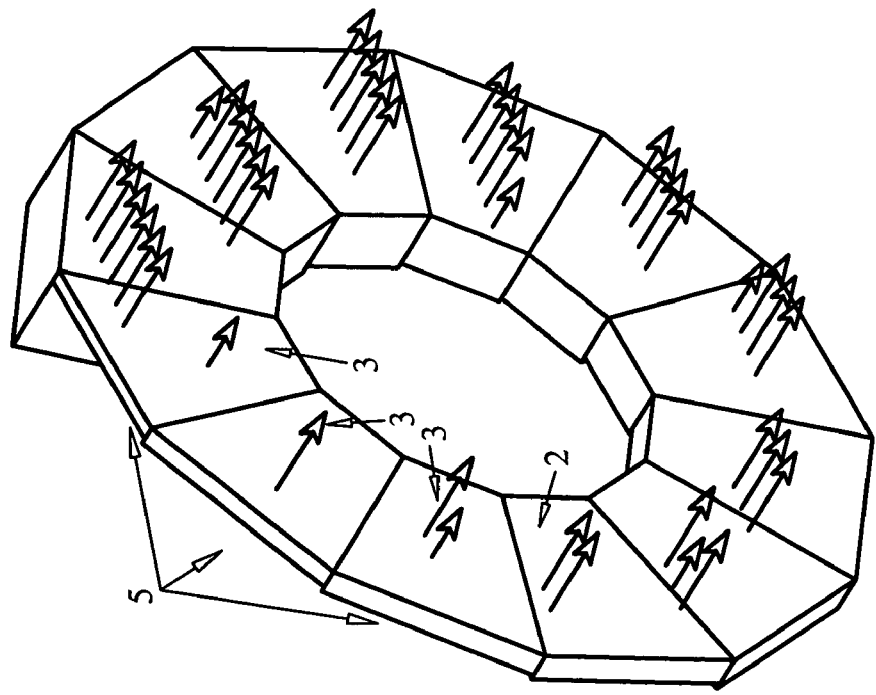
FIG. 2 is a perspective view of the individual magnets of the disk like member shown in FIG. 1.
Figure 1:
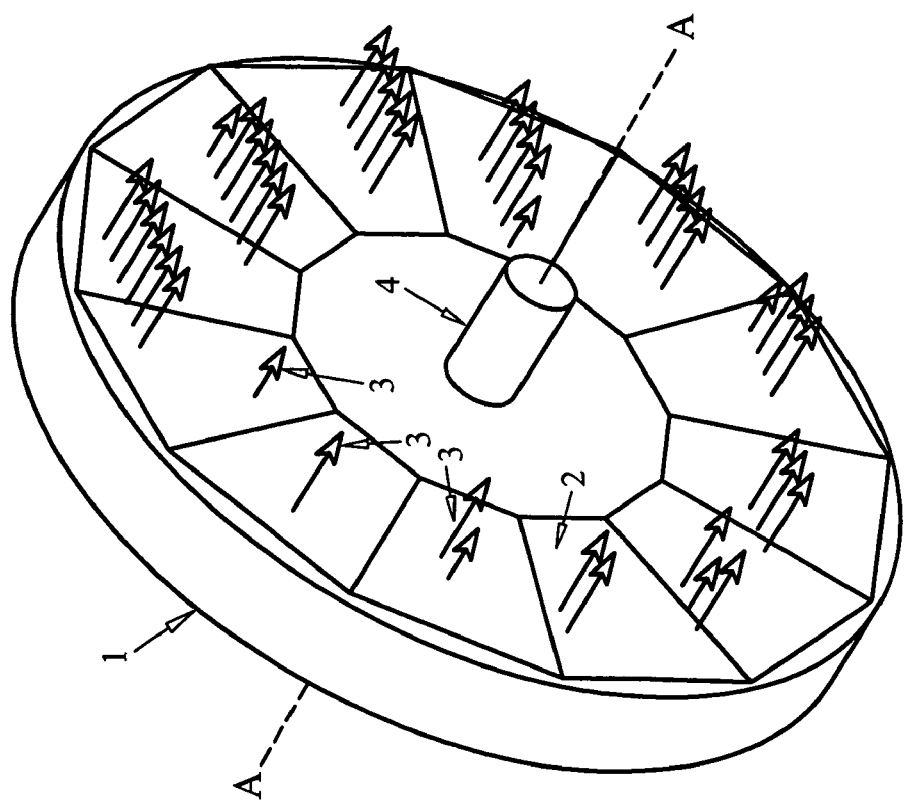
FIG. 1 is a perspective view of a rotating disk like member.

Reference will now be made in detail to the present preferred embodiments of the invention, examples of which are illustrated in the accompanying drawings. Wherever possible, the same reference numbers will be used throughout the drawings to refer to the same parts.

The present invention creates an induced DC-like electric field in biological material to treat the material. The biological material can be portions of a living human or animal, such as body fluids, cells, tissue, or bone.

The induced DC-like electric field can treat the biological material in numerous ways, including promoting regeneration of damaged tissue. For example, the DC-like electric field can treat trauma (e.g., bruises, torn muscles, and cartilage damage); debilitation; organs by stimulating their regeneration to restore their functions; damaged or severed human nerves or axons; slow or non healing bone fractures (nonunions); occlusion of blood flow due to formation of plaque or other forms of calcification in the blood stream; ailments such as heart disease and senility, resulting from reduced blood flow to the affected organ; or osteoporosis (both prevention and reversal).

The induced DC-like electric field also can treat the biological material by destroying it or disrupting its normal processes. For example, cancerous tissues within the human body can be treated by inducing high electric currents.

The induced DC-like electric field also can be used to increase migration of electrically charged materials through the biological material. For example, the induced DC-like electric field can enhance transdermal transport of efficacious ionic drug components to specific locations within the tissue, thus reducing the amount of drug needed as well as toxic effects from the drug.

The induced DC-like electric field also can decrease human nerve pain by blocking electrical signals along nerve paths.

The present invention induces a DC-like electric field in the biological material by subjecting it to a stepwise time changing magnetic field. Ions exposed to a time changing magnetic field are subject to a force that will produce electric currents that will oppose the change in the magnetic field. The general law for the electric field associated with a changing magnetic field is the vector equation: $\Delta \times E = -\partial B/\partial t$, where E is the vector electric field and B the vector magnetic field.

The semi-conducting biological tissue will allow the flow of electric current within the tissue. In order to induce an EMF (Electro Motive Force) capable of charge transport, the induced magnetic field must conform to certain parameters. The magnetic field must be asymmetric and have the necessary and sufficient exposure time, magnetic field strength and time rate of change to induce currents that will produce a transport of electric charge greater than 0.1 Coulombs/cm$^2$ that has been shown to be a necessary requirement for therapeutic application of electric fields. It is well known by medical researchers and medical practitioners that DC-like electric currents of strengths between 0.000001 A and 0.001 A can be of significant benefit in causing trauma healing to bone, nerve, and other tissue.

The present invention teaches an improved method for producing a powerful and quickly repetitive DC like electric field by continuously changing the magnetic field.

Embodiments of the invention using the first method of producing a stepwise changing magnetic field are depicted in FIGS. 1-5. In accordance with this aspect of the invention, the present invention includes at least two permanent or electromagnets for creating a stepwise changing magnetic field that can pass through the biological material, and a drive mechanism for moving the magnets relative to the material to induce a DC-like electric field within the material with the stepwise changing magnetic field.

As embodied herein, the permanent magnets for creating the stepwise changing magnetic field are rare earth magnets 2, having a coercivity of greater than 1 kOe. Preferably, the magnets 2 are neodymium-iron-boron (Ne$_2$ Fe$_{14}$ B). However, other permanent magnets of lesser strength can be used.

The embodiments of the invention disclosed and explained herein that practice the first method of moving a stepwise changing magnetic field use permanent magnets. However, the invention can also be carried out by replacing the permanent magnets with stepwise changing electromagnets. Any conventional electromagnets can be used that have the required strength. The electromagnets should be connected by conventional connections to a power source.

As embodied herein, the stepwise changing magnets 2 are mounted in a circular pattern in slots on the face of disk-like member 1. The stepwise changing magnets 2 are set into disk-like member 1 near the outer periphery of disk 1 so that all the outer surfaces of magnets 2 are aligned with and parallel to a single circular face of disk-like member 1. Each magnet 2 is connected, preferably with a suitable adhesive, in closely machined indentations on the circular face of the cylinder 1 so that they form a flat surface. Each magnet 2 preferably is glued into each slot with high quality glue. However, other conventional connectors can be used.

To achieve DC-like current, or "square wave" voltage each magnet 2 is arranged in a stepwise manner so that, looking at the surface of the magnets and proceeding in a counter-clockwise direction, each adjacent magnet has a constant magnetic field strength represented by arrows 3. The smallest arrow 3a indicates a vector magnetic field of B. While Thus, the magnetic field strength of the first and weakest magnet is B, the next 2 B, the next 3 B, and so on. The magnets are all polarized with the same polarity parallel to axis, A-A of the disk-like member 1. Disk-like member 1 is mounted on a shaft 4 parallel to axis A-A that can be driven.

In the preferred embodiment, the permanent magnets 2 have varying depth or thickness 5 as shown in FIG. 2. Each magnet 2 is fitted into closely machined slots in disk-like member 1, which allow for the varying depth or thickness 5.

Figure 3:
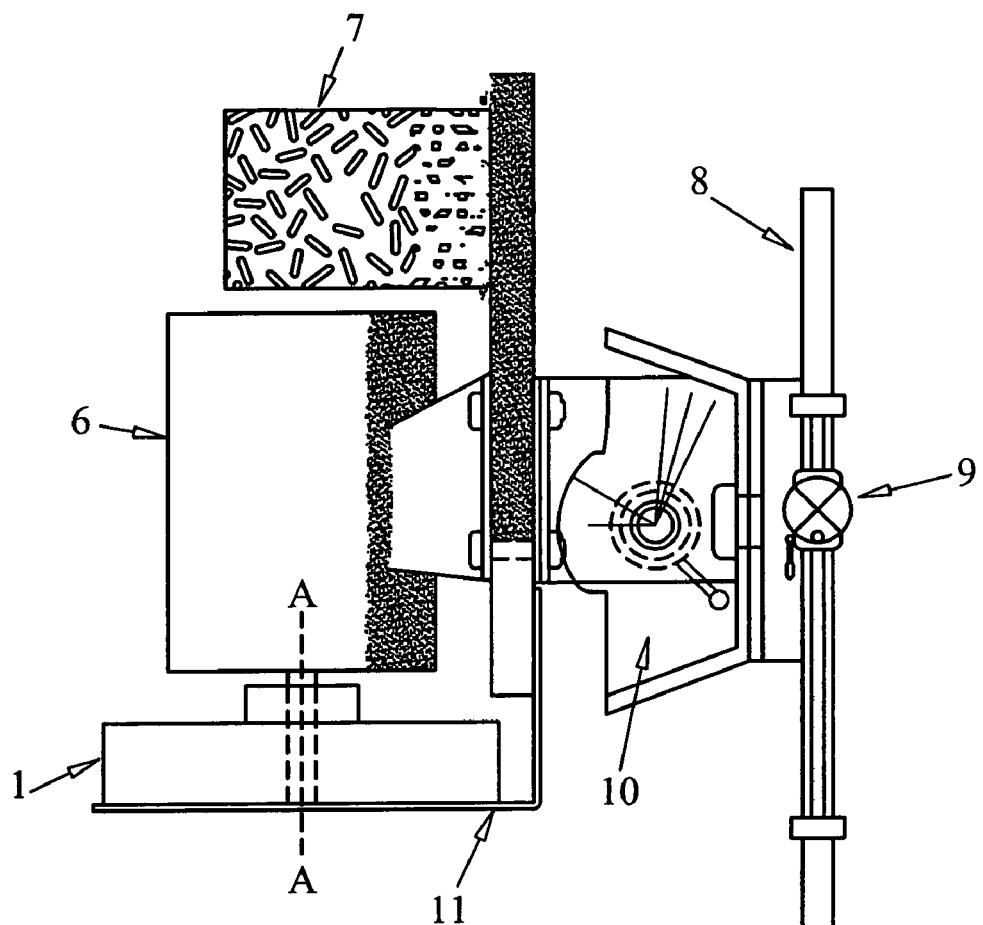
FIG. 3 is a plan view of a motor driven treatment system using the rotating disk like member.

In the embodiment shown in FIG. 3, the disk-like member 3 is driven by a conventional electric or mechanical drive motor 6 connected to a speed control device 7. The speed control device 7 is adjustable through a wide range of rotary speeds and thereby can adjust the induced current strength. The rotation of the motor 6 is translated to the disk-like member 1 by the shaft 4. The angle of the outer magnetic face of the disk-like member is controlled by a dual axis assembly 10. The outer magnetic face of the disk-like member 1 is separated from the treated biological material by a protective guard 11. The protective guard 11 made of a non-conducting material such as glass-reinforced plastic or some other non-magnetic and non-conducting plastic. A gear track 9 mounted on a stand 8 controls the height of the outer magnetic face of disk-like member 1.

Figure 4:
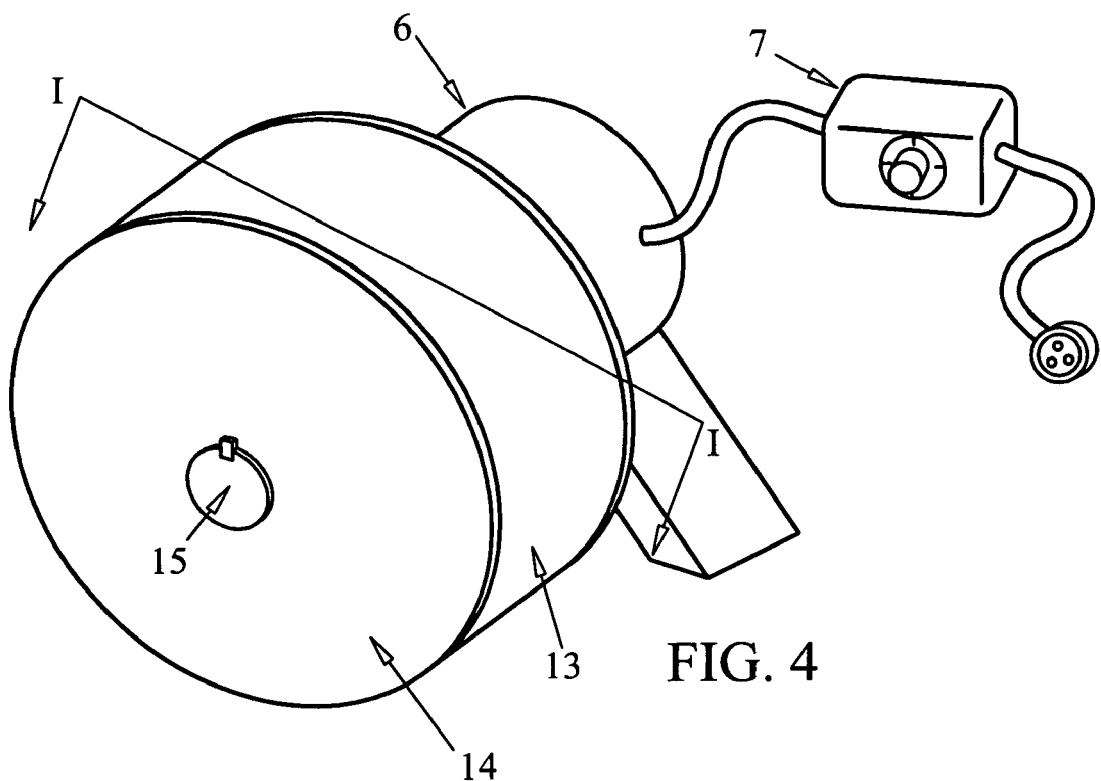
FIG. 4 is a perspective view of an alternate embodiment of the rotating disk like member utilizing a plurality of permanent magnets forming a portion of the outer peripheral surface.

In another embodiment shown in FIG. 4, permanent magnets 13 are mounted on the rim or outer peripheral surface of the disk-like member 14. The disk-like member 14 is mounted on a shaft 15 and driven by motor 6 with a rotary speed controlled by speed controller 7.

Figure 5:
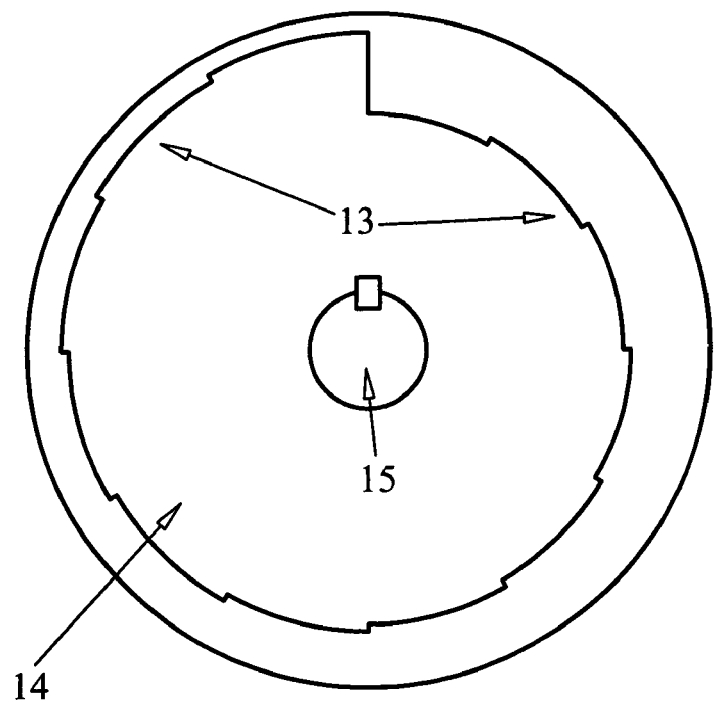
FIG. 5 is a cross-sectional view of the disk like member of FIG. 4 taken along line I-I.

FIG. 5 is a sectional view taken along line I-I of FIG. 4. FIG. 5 shows a section of the disk-like member 14. In the embodiment, the stepwise change in magnetic field strength is created by the changing radial thickness of each magnetic segment 13. Each magnetic segment 13 has a polarity of a north pole facing radially outward from the center of in disk-like member 14. Preferably, the magnets 13 are glued into closely machined slots in disk-like member 14 although other attachments may be used.

The rotation of disk-like member 14 produces a stepwise changing magnetic field near the outer rim surface. The rate of rotation will determine the time rate of change of the magnetic field and thus the strength of the induced electric field is proportional to the R.P.M. (Revolutions Per Minute) of the disk-like member 14.

Figure 6:
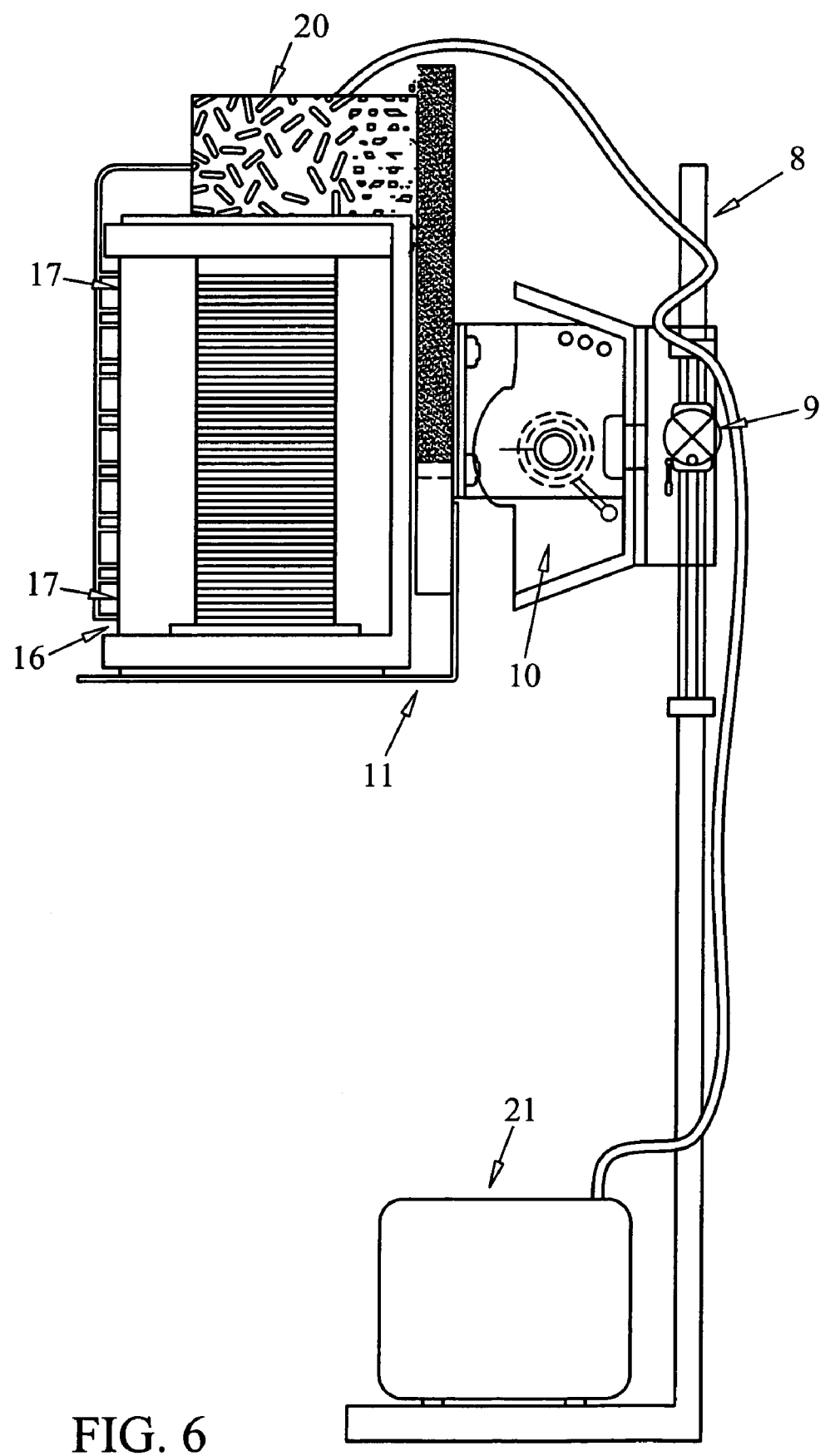
FIG. 6 is a perspective view of an alternate embodiment with an electromagnet generates a stepwise changing magnetic field.

FIG. 6 shows a further preferred embodiment. This preferred embodiment produces a stepwise changing magnetic field with electromagnet coils 17 mounted on a core 16. In this embodiment, the plurality of electromagnet coils 17 are progressively energized by switches 19 in a time sequence by controller 20. The progressive increase in the number of amp-turns of coils 17 that are energized by the application of the electric power through timer and switches 19 produces a steady increase in the magnetic field 18.

Figure 7:
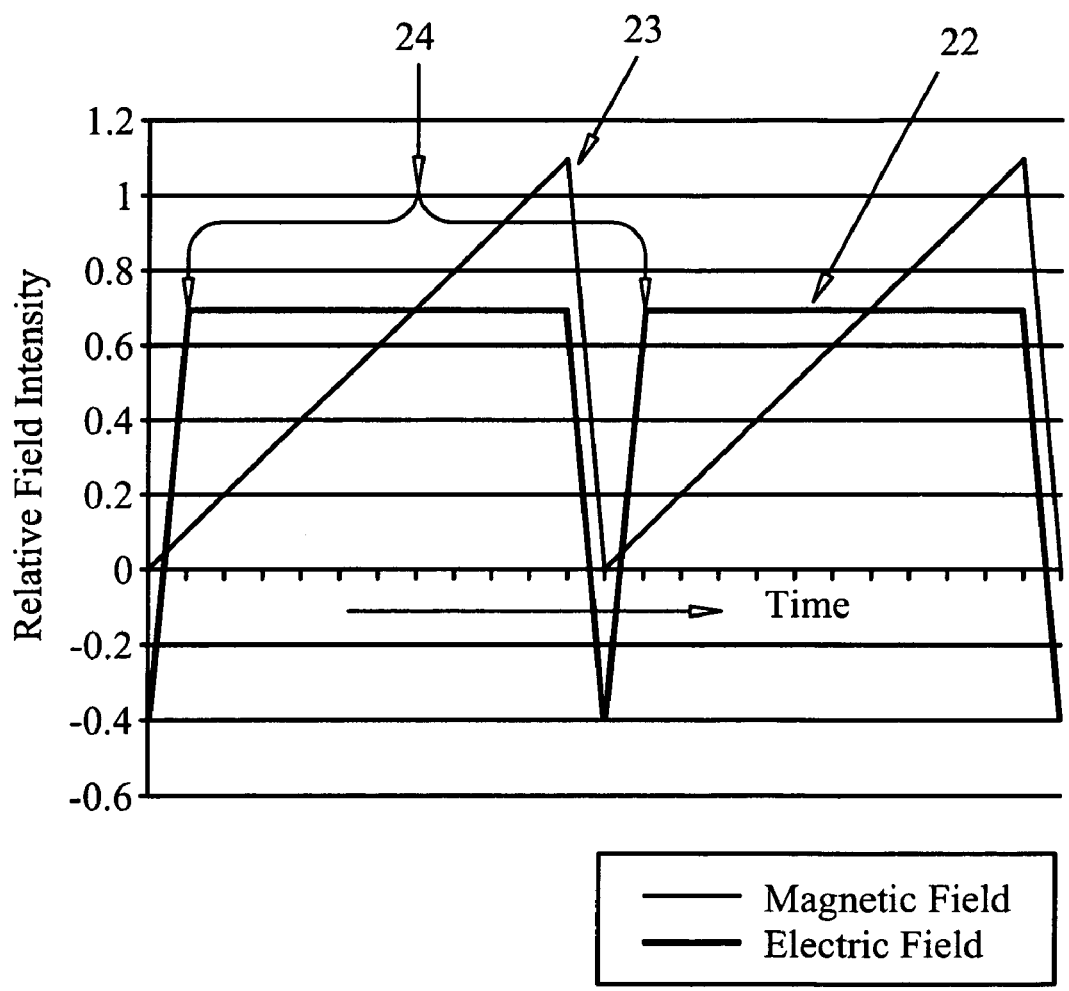
FIG. 7 is a graph plotting the magnetic and resultant electric fields generated by all the embodiments of this invention versus time.

FIG. 7 is a graph plotting the magnetic field 23 and the resulting electric field 22 plotted versus time through two cycles 24. Any semi-conducting biological material that is suffused by the magnetic field 18 will support electric currents that are driven by an induced electric field 22. The resulting induced DC-like electric field 22 will produce charge transport in the semi-conducting medium. The frequency of this electric field as indicated by time of one cycle 24 is not less than 50 Hz and not greater than 1000 Hz.

FIG. 6 shows a typical embodiment for the therapeutic application. Power supply 21 energizes coils 17 on core 16 5 through controller 20. The angle of the outer magnetic face of the core 16 is controlled by a dual axis assembly 10. The outer magnetic face core 16 is separated from the treated biological material by a protective guard 11. The protective guard is made of non-conducting material such as glass-lO reinforced plastic or some other nonmagnetic and nonconducting plastic. The height of the outer magnetic face of core 16 is controlled with gear track 9 mounted on stand 8.

Other embodiments, not shown, would allow a single coil 17 to produce a DC-like electric field 22 if the singular coil 17 is energized by a continuously increasing electric field that would produce a continuously increasing magnetic field such as shown in FIG. 7.

Another embodiment, not shown, shapes the magnetic core 16 or includes magnetic shielding materials to focus or confinement of the magnetic field 18. The judicious use of such well known technologies by one skilled in the art would allow the increase of magnetic filed intensity in the treatment volume of the biological material.

In a further embodiment, the apparatus includes a transporter for moving at least one medicant to humans and animals through a transdermal site. The apparatus includes a medicant supply located on the site and at least one stepwise changing set of permanent magnets in proximity to the site. A drive mechanism is disposed to move the magnets relative to the site to induce a DC-like electric field with in the site, the electric field being of sufficient magnitude to increase the rate of transportation of the medicant.

Figure 9:
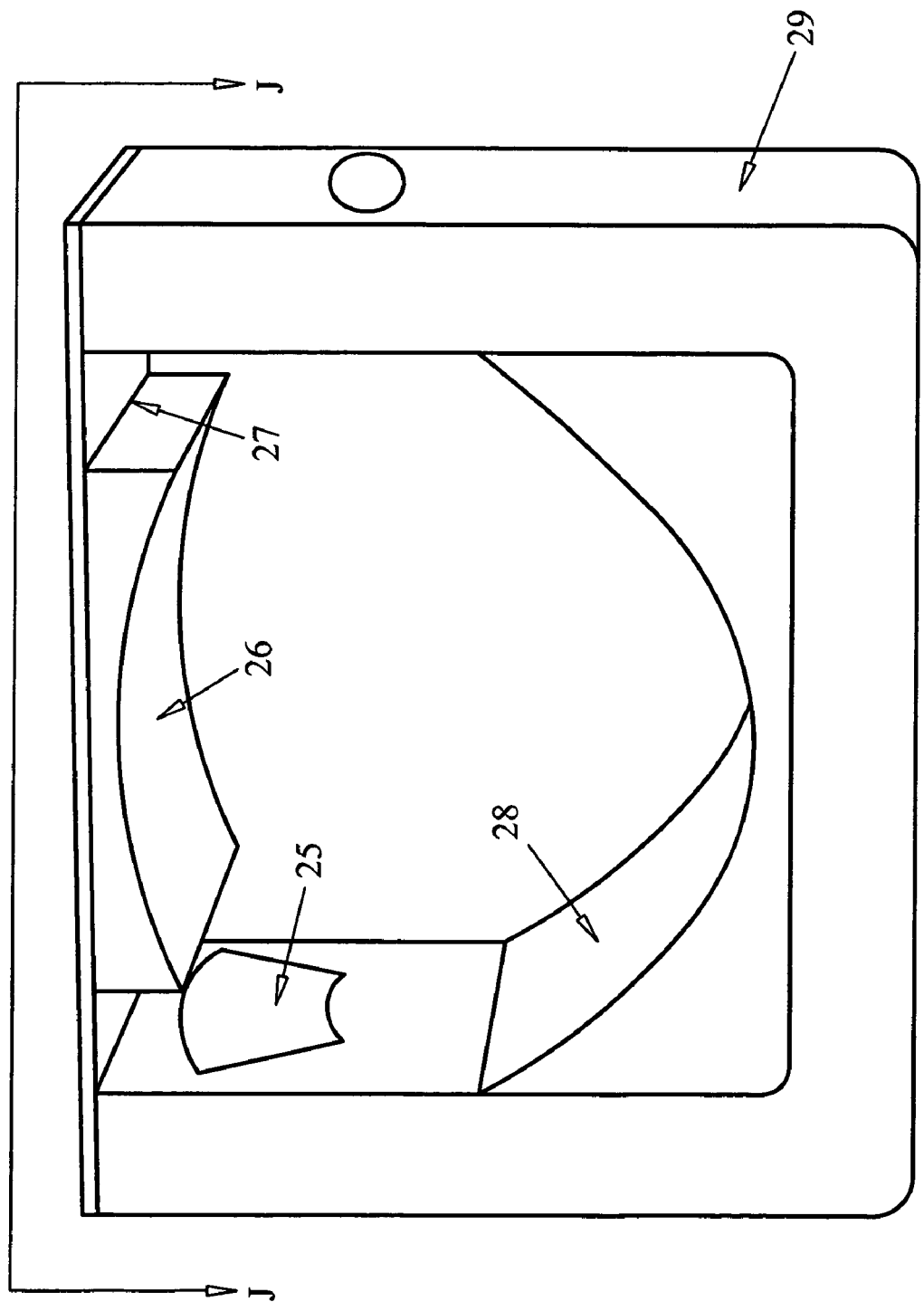
FIG. 9 is a perspective view of a transdermal medicant delivery device using a stepwise changing magnetic field to induce the transport of the medicant.
Figure 10:
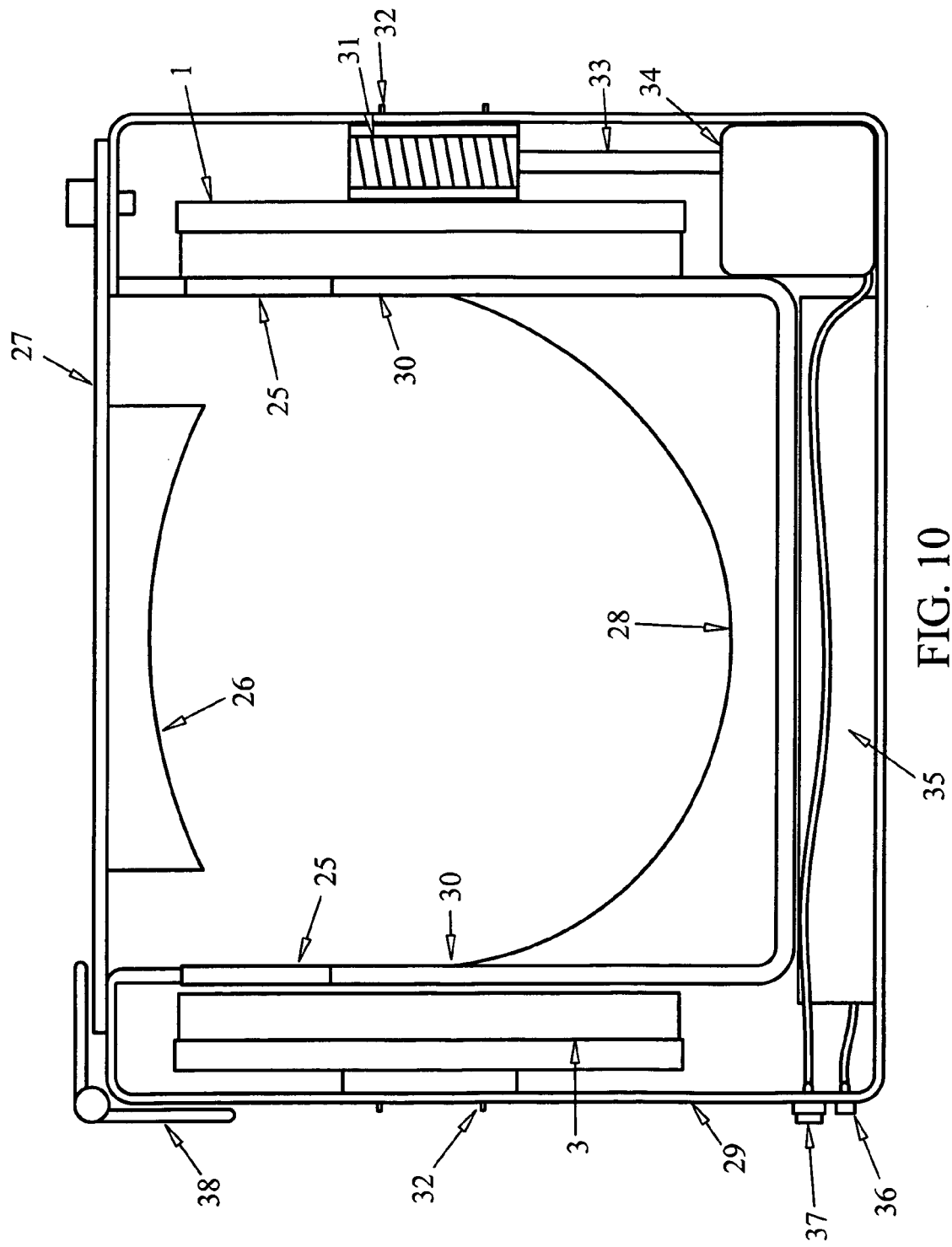
FIG. 10 is a cross-sectional view of FIG. 9 taken along line J-J.

As embodied herein, the medicant supply is a drug-saturated pad 26 that can be held in place against the surface of the biological material. As shown in FIGS. 9 and 10, the portable transdermal drug induction system 29 includes a plate 27 for holding the drug-saturated pad 26. The plate 27 rotates on hinge 38 to allow the placement or removal of the pad 26.

As embodied herein, the permanent magnets 3 mounted on disk 1 rotate on bearings 32. The permanent magnets 3 are mounted so that magnets 3 of equal strength but opposite polarity face each other across the encased volume. Thus, the magnetic field exiting magnetically transparent windows 25 is in a single direction at all times and is attractive at all times. One of the disks is driven by drive mechanism 32 mounted on a shaft 33 driven by electric motor 34. A second drive mechanism 32 may be used on the opposite magnetic disk. The speed of the electric motor 34 is varied by a controller 37 and powered by batteries 35, which may be recharged via a connection 36.

The limb or body portion is placed between drug pad 26 and a cushion 28 so that the skin surface is located in the plane between magnetically transparent windows 25 located within the magnetic shielding material 30. The stepwise time changing magnetic filed exiting from magnetically transparent windows 25 and emanating form the opposite magnetic pole surfaces of the disk-like member 1 transects both the drug saturated pad 26 and the dermal regions of the encased biological material. The magnetically generated induced DC-like electric field causes ionic forms of the drug held in the pad 26 to penetrate the skin and tissue of the limb or body portion enclosed between the drug pad 26 and the cushion 28.

One or both disks 1 are driven by the electrical motor 34. The controller 37 with a variable speed adjustment allows a wide assortment of rotary speeds, direction of rotation, and times of operation.

In the preferred embodiment, the rotation or the driven disk 1 causes the facing magnet of opposite polarity freewheeling on bearing shaft 32 to rotate.

A housing 29 encloses the unit. The inner surfaces of the housing 29 that are most proximate and parallel to the outermost faces of the magnetic disks are covered by the magnetic shielding 30, which prevents the passage of the magnetic field except through such openings as are provided. The magnetic shielding preferably has two annular opening that allow the magnetic field to exit the housing surfaces and cause transdermal transport of the cations or anions of various drugs through the surface of the skin of the enclosed limb.

In a further embodiment of the present invention, an apparatus transporting at least one medicant to humans and animals through a transdermal site. The apparatus includes a medicant supply located on the site and electromagnets in proximity to the site. A control device is disposed to apply stepwise increasing current to the electromagnets to generate a stepwise changing magnetic field through the transdermal site thereby inducing a DC-like electric field within the material in proximity to the site, the electric field being of sufficient magnitude to increase the rate of transportation of the medicant. This embodiment of the invention is similar to that shown in FIGS. 9 and 10 but employs electromagnets of the type shown in FIG. 6 instead of permanent magnets.

Each of the above embodiments and numerous other possible configurations are based on the concept of a stepwise changing magnetic field generating an electric current in or on a biological material without the use of electrodes. Stepwise changing magnetic fields of up to 2000 gauss can be achieved by both permanent and electromagnets. Rates of change for fields generated by both permanent and electromagnets can be achieved using standard methods of movement or electronic switching or electric current modulation. The systems can meet or exceed all existing invasive therapeutic devices using direct electric stimulation. The systems preferably generate an electric field strength in the biological material in the range of 1 mV/cm to 10000 mV/cm (millivolts per centimeter). The systems can also preferably generate a DC-like electric current in the biological material in the range of 0.000001 amperes to 10.0 amperes. Thus, the present invention generates DC-like electric currents for medical treatment while elimination the risk to the patient caused by inserting electrodes.

FIGS. 11-16 show an embodiment of the invention that utilizes an electromagnetic coil connected to a dual circuit to produce the saw-tooth shaped magnetic field having a sufficient duty cycle and strength to move charge (i.e. dB/dt) by inducting a "DC-like" electrical current in the tissue being treated.

Figure 11:
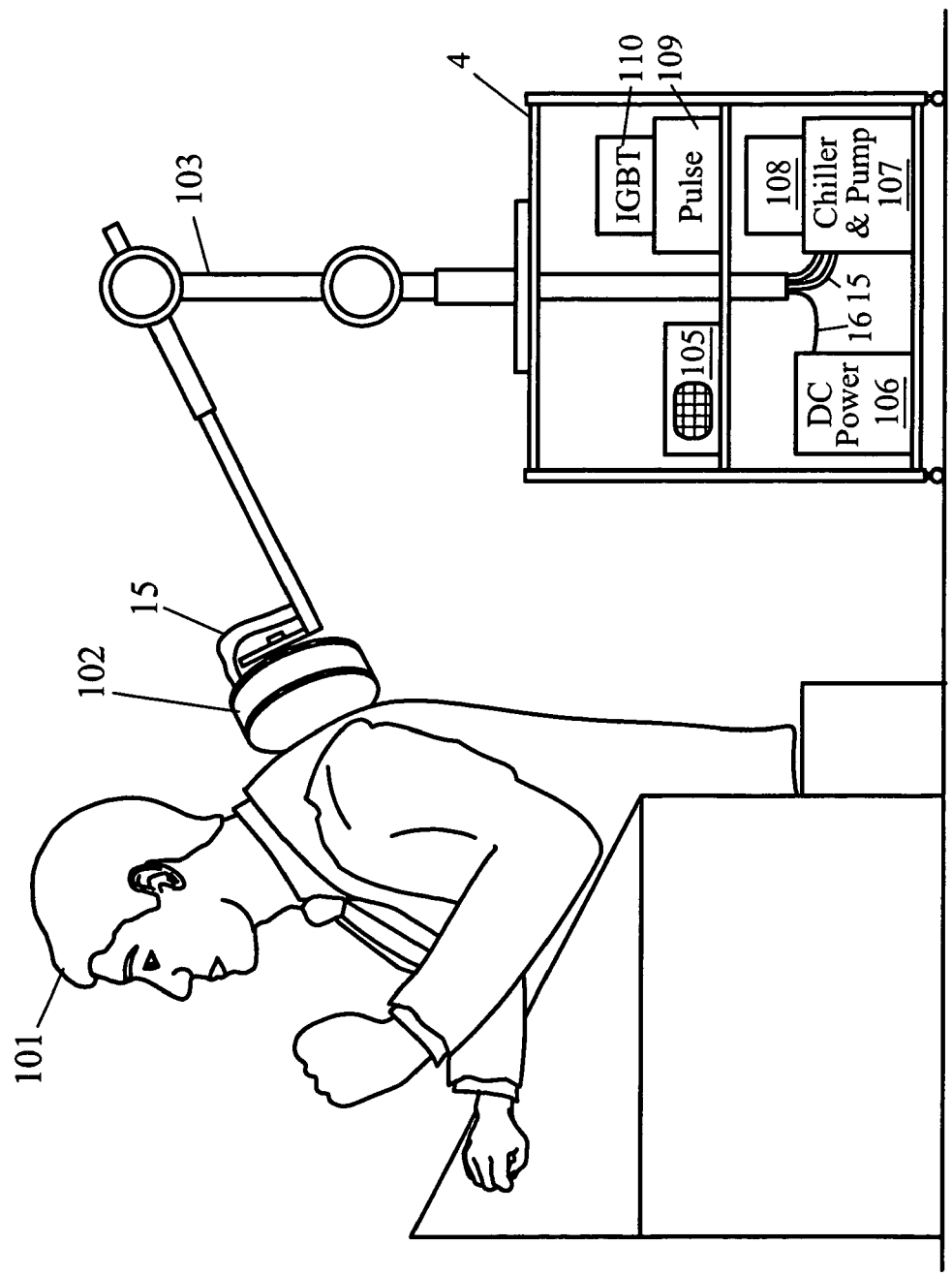
FIG. 11 is a diagrammatic front view of an electromagnetic coil embodiment of the apparatus according to the invention.

FIG. 11 shows a coil treatment head 102 of sufficient numbers of turns and dimensions to fit the desired application. The structural components 103 (i.e. the non-electrical components) are preferably made from a non-conductive material in order to avoid heating due to induced electric currents and vibration noise also due to induced currents. The coil embodiment includes a DC power supply 106, an electronic monitor 105, a chiller and pump 107 for cooling and moving liquid coolant to and from the coil treatment head 102, a cart table 104, a protected resistor bank 108, a pulse generator 109, an IGBT with ancillary power supply and subsystems 110, cooling tubes 115, and wiring 116.

Figure 12:
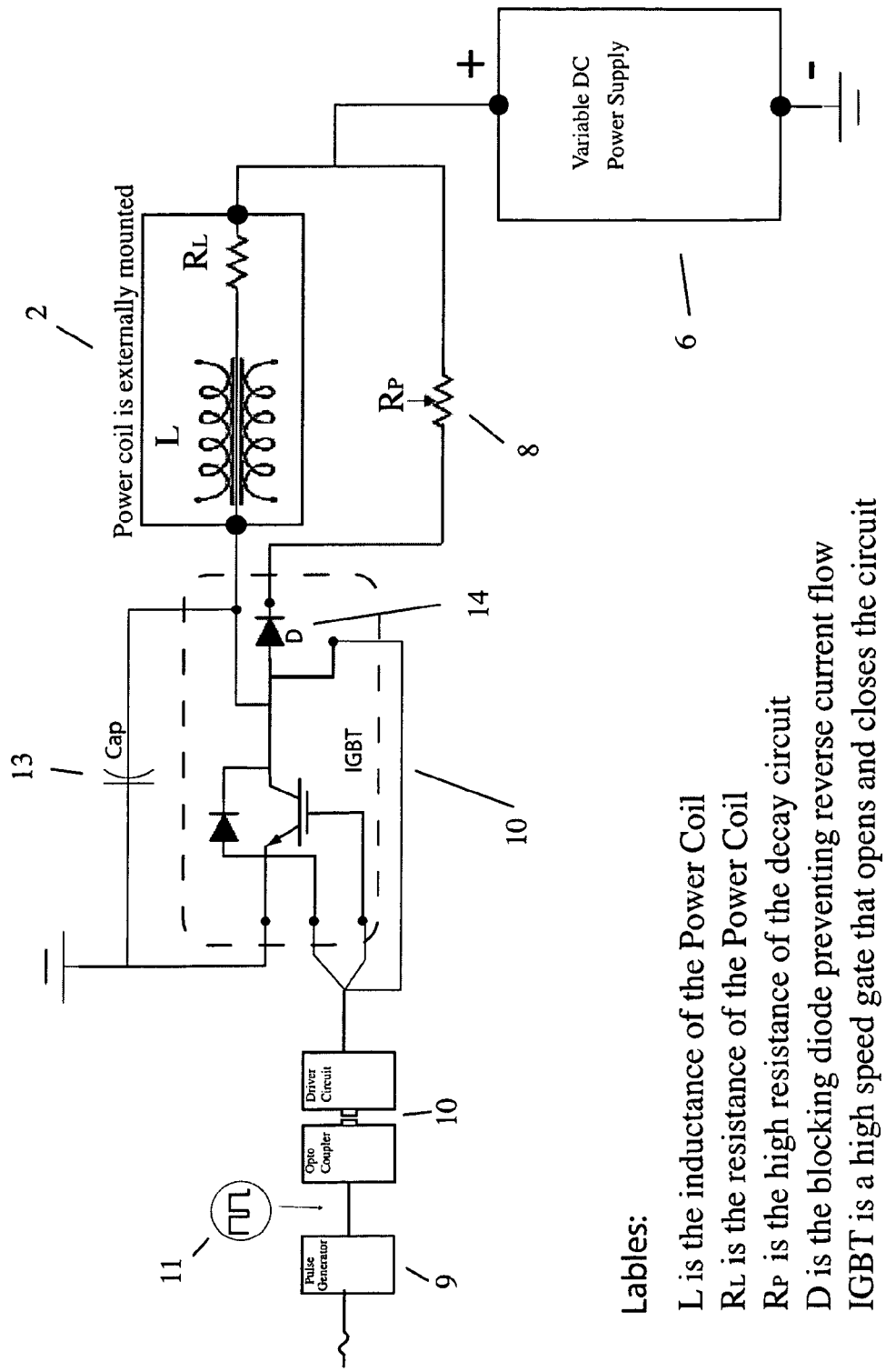
FIG. 12 is a block diagram of the electromagnetic coil embodiment of the apparatus.

In the coil embodiment of the apparatus, a power circuit of the type shown in FIG. 12 is employed. This "dual circuit" can be switched between two modes: i.e. the circuit shown in FIG. 13A and the circuit shown in FIG. 13B. The difference between the circuits being that the IGBT switches back and forth between ground (FIG. 13A) and the ballast resistance 108 (FIG. 13B).

In a working example of the coil embodiment, a typical setting for the DC power supply 106, the DC power supply would provide DC current and voltage of 18 A and 70 V. This power can be increased or decreased as warranted by application.

Figure 14A:
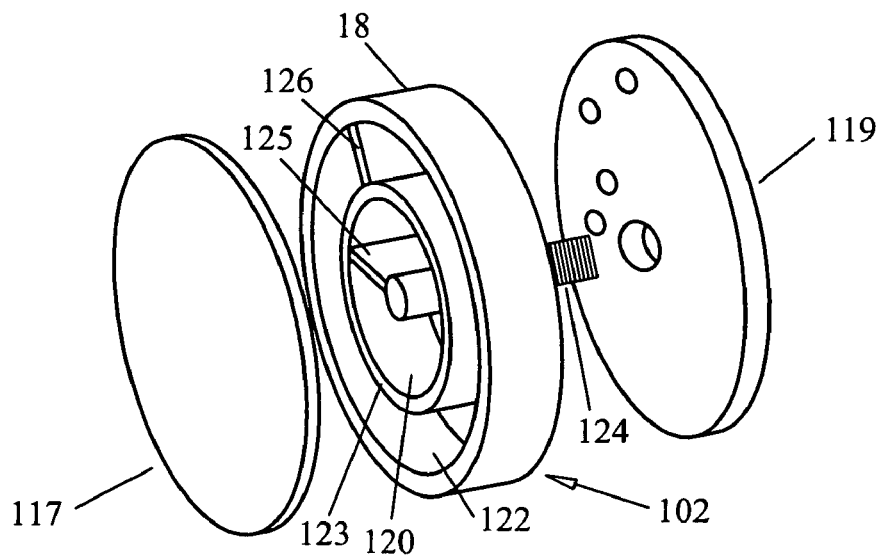
FIG. 14A is a perspective exploded view of the coil.
Figure 14B:
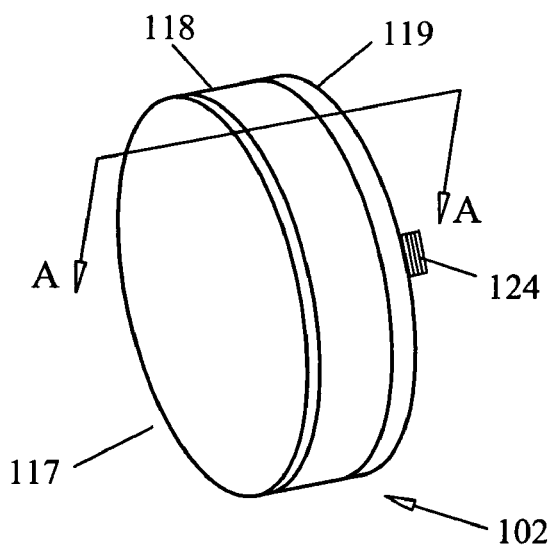
FIG. 14B is a perspective view of the coil.
Figure 14C:
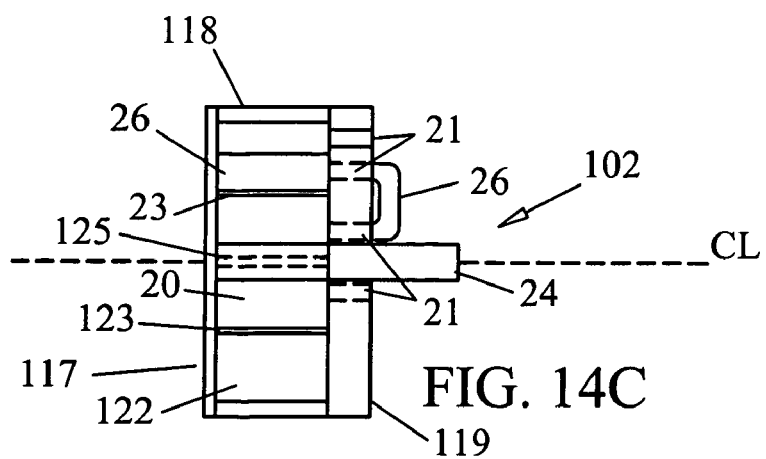
FIG. 14C is a section view of the coil taken along line A-A in FIG. 14B.

In the coil embodiment, a coil treatment head 102 of the appropriate number of turns, dimensions, and shape to provide effective treatment is encased in a cooling system of the type illustrated in FIGS. 14A, 14B, and 14C. A typical example is coil of number twelve-gauge wire wound with ninety turns on a cylindrical core of twelve centimeters (12 cm) diameter and a length of three centimeters (3 cm).

Figure 15A:
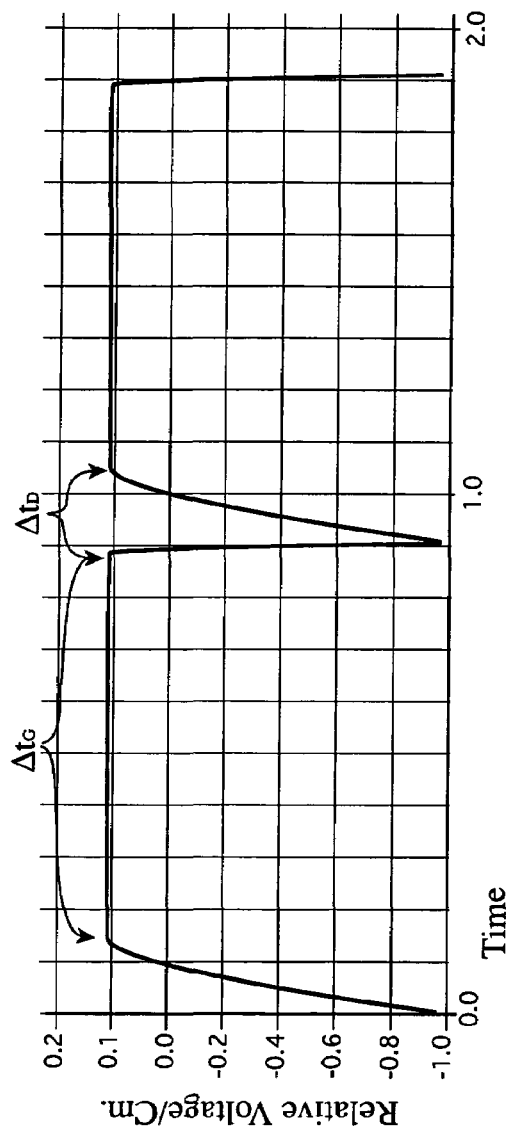
FIG. 15A is a graph plotting relative voltage per centimeter of the coil versus time.
Figure 15B:
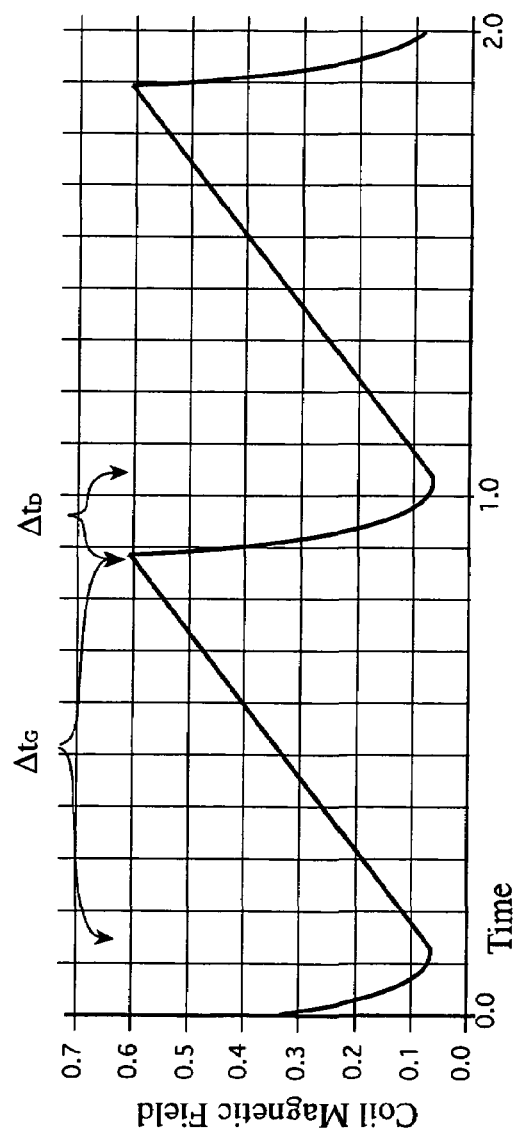
FIG. 15B is a graph plotting magnetic field strength of the coil on the same time axis as FIG. 15A.

In the preferred embodiment components and settings are chosen to produce a continuously repetitive magnetic and induced electric fields such as those shown in FIGS. 15A and 15B. A typical setting would produce induced electric fields of 20 mV/cm at 3 cm above the face 117 of the coil and within the diameter of the coil windings 123. A typical setting would produce a Duty Cycle of 88%. Using the times for each part of the cycle indicated in FIGS. 15A and 15B, Duty Cycle=$(\Delta t_G/(\Delta t_G+\Delta t_D))*100$=88%. At no time should the Duty Cycle be less than 30% otherwise the minimum threshold charge transfer (rate) will not be induced and no therapeutic effect akin to a direct current will result.

FIG. 11 shows an electromagnetic coil embodiment of the invention being used in the treatment of a patient 101. The coil treatment head 102 is mounted on an adjustable arm 103 and controlled by the subsystems (electronic monitor 105, DC Power 106, Chiller and pump 107, resistor bank 108, pulse generator 109, and IGBT 110).

FIG. 12 shows the basic power circuit. It includes the coil treatment head 102 powered by a DC power supply 106. The power to the coil 102 is switched by the IGBT 110, between ground and ballast resistance 108. The timing of the switching sequence is controlled by the pulse generator 109 and the IGBT with ancillary power supply and subsystem 110.

Figure 13A:
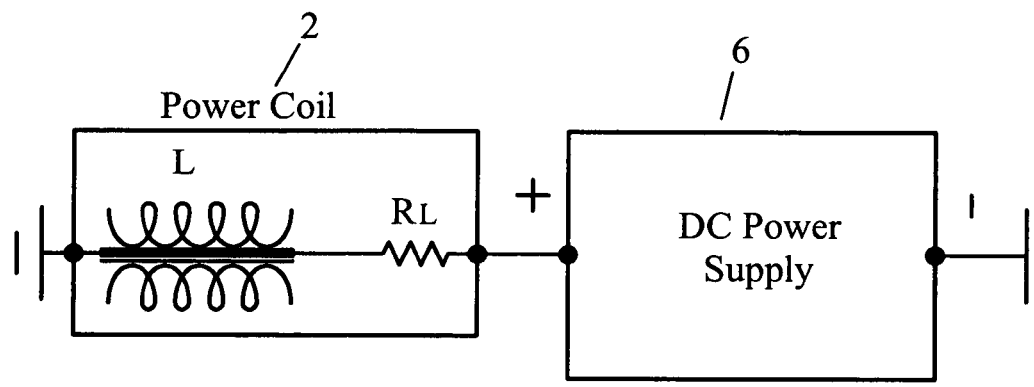
FIG. 13A is a block diagram showing a circuit of the electromagnetic coil embodiment connected to ground during the charging part of the cycle.
Figure 13B:
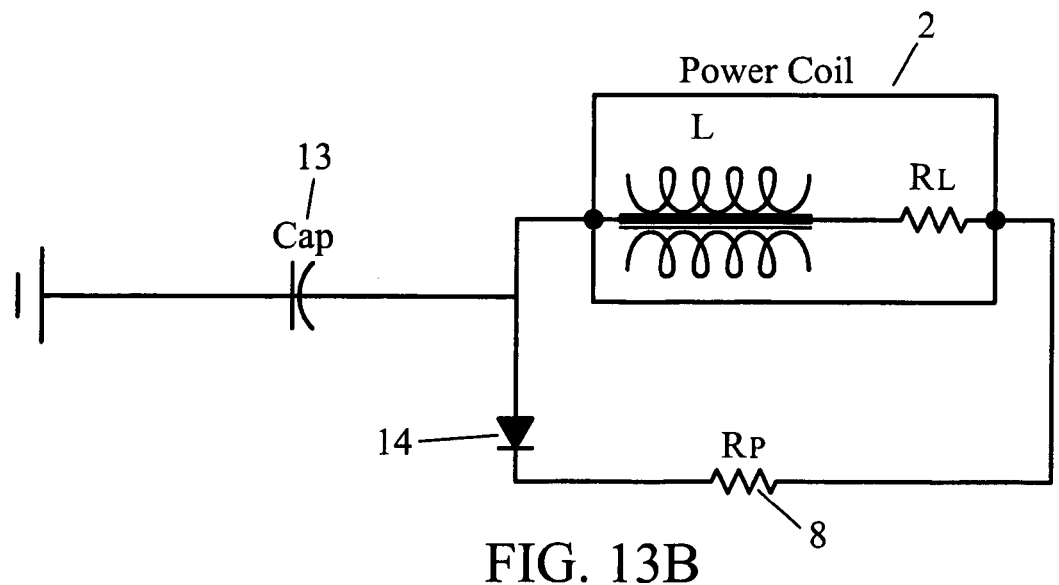
FIG. 13B is a block diagram showing the circuit disconnected to the ground and connected through a ballast resistance during the discharge part of the cycle.

FIG. 13A is the circuit as it functions when the coil is connected to ground and is being charged.

FIG. 13B is the circuit as it functions when coil is not connected to ground but through the ballast resistance 108 in a closed loop and is being discharged.

FIG. 14A is the exploded view of a typical construction for a liquid-cooled coil treatment head 102. It shows an inner cooling channel 120 and an outer cooling channel 122. The inner and outer cooling channels each have baffles 125 and 126 to direct the flow of a cooling liquid pumped through the inner and outer cooling channels 120 and 122. Holes 121 conduct the cooling liquid to and from the channels 120 and 122. The coil windings 123 are encased between the cooling channels 120 and 122. A cylinder 118 and end plates 117 and 119 encase the coil windings 123. A stud 124 connects the coil treatment head to a mount.

In an alternate embodiment that is not shown in the drawings, the coil can be made from conductive (i.e. copper) tubing. To cool the tubular coil, coolant can be pumped through the tubes.

FIG. 14B is the orthographic view of the coil treatment head 102. Section A-A indicates a view of a section taken through the central axis of the coil.

FIG. 15A is an oscilloscope trace of the actual voltage generated in a sensor within range of the electric field of the coil treatment head 2. Segment $\Delta t_G$ of the signal is generated by the rising magnetic field of the treatment coil produced by a rising current in the coil windings. Segment $\Delta t_D$ is the voltage signal during the decay and recovery time for the current and magnetic field of the coil treatment head 102.

FIG. 15B is a representation of the magnetic field strength in the volume of space above the face 117 of the coil treatment head 102 approximately parallel to the axis (i.e. the stud 124) of the coil treatment head 102.

Figure 16:
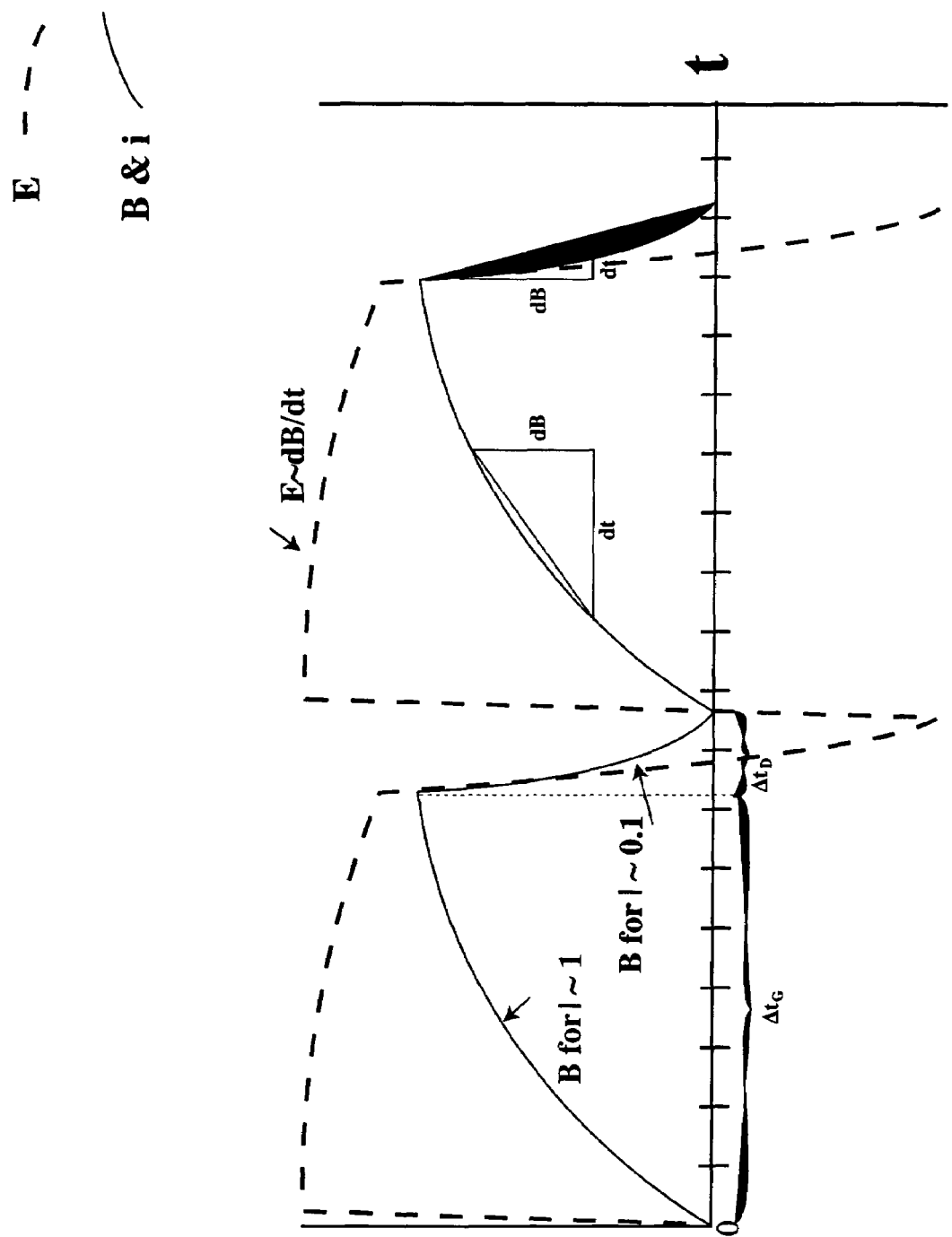
FIG. 16 is a graph plotting typical magnetic and electric field strengths of a coil versus time.

FIG. 16 is a graph plotting typical magnetic and electric field strengths of a coil vs. time. It illustrates the growth and decay rates for L/R ratios of ~1 and ~0.1.

It will be apparent to those skilled in the art that various modifications and variations can be made in the present invention without departing from the scope or spirit or the invention. Other embodiments of the invention will be apparent to those skilled in the art from consideration of the specifications and practice of the invention disclosed herein. It is intended that the specification and examples be considered as exemplary only, with a true scope and spirit of the invention being indicated by the following claims.

I claim:

1. An apparatus for creating therapeutic charge transfer in tissue, comprising:
    a coil generating a changing magnetic field to induct an electric field in the tissue exceeding 10 mV/cm when said coil is 5 cm from the tissue, said magnetic field having a growth phase and a decay phase, a duration of the growth phase being at least ten times a duration of the decay phase; and
    a control circuit controlling a current fed to said coil, said control circuit including two subcircuits and a switch for switching between a first of said subcircuits and a second of said subcircuits, said first of said subcircuits causing said growth phase, said second of said subcircuits causing said decay phase;
    each one of said subcircuits having a respective time constant ($\lambda$) equaling an inductance (L) divided by a resistance (R) of said respective one of said subcircuits; and
    said $\lambda$ of said second subcircuit being at least ten times said $\lambda$ of said first subcircuit.

2. The apparatus according to claim 1, wherein said magnetic field is saw-tooth shaped.

3. The apparatus according to claim 1, wherein said first subcircuit has a $\lambda$ no greater than 1, $\lambda$ being calculated by dividing a resistance (R) of said first subcircuit by an inductance (L) of said first subcircuit.

4. The apparatus according to claim 1, wherein said coil is configured to receive a voltage exceeding 2000 V.

5. The apparatus according to claim 1, wherein said coil is liquid cooled.

6. The apparatus according to claim 5, wherein said coil is cylindrical and has an inner channel and an outer channel through which coolant can be passed to cool said coil.

7. The apparatus according to claim 1, wherein said magnetic field has an asymmetric waveform.

8. The apparatus according to claim 1, wherein said coil generates a changing magnetic field to induct an electric field in the tissue exceeding 10 mV/cm when said coil is 5 cm from the tissue.

9. An apparatus for creating therapeutic charge transfer in tissue, comprising:
    a coil generating a changing magnetic field to induct an electric field in the tissue exceeding 10 mV/cm when said coil is 5 cm from the tissue, said magnetic field having a growth phase and a decay phase, a duration of the growth phase being at least ten times a duration of the decay phase; and
    a control circuit controlling a current fed to said coil, said control circuit including two subcircuits and a switch for switching between a first of said subcircuits and a second of said subcircuits, said first of said subcircuits causing said growth phase, said second of said subcircuits causing said decay phase;
    said second subcircuit having a time constant ($\lambda$) no less than 10, $\lambda$ being calculated by dividing a resistance (R) of said second subcircuit by an inductance (L) of said second subcircuit.

10. An apparatus for creating therapeutic charge transfer in tissue, comprising:
    a coil generating a changing magnetic field to induct an electric field in the tissue exceeding 10 mV/cm when said coil is 5 cm from the tissue, said magnetic field having a growth phase and a decay phase, a duration of the growth phase being at least ten times a duration of the decay phase; and
    a control circuit controlling a current fed to said coil, said control circuit including two subcircuits and a switch for switching between a first of said subcircuits and a second of said subcircuits, said first of said subcircuits causing said growth phase, said second of said subcircuits causing said decay phase;
    said second subcircuit including an Integrated Gate Bipolar Transistor (IGBT) for increasing a resistance of said second subcircuit.

11. An apparatus for creating therapeutic charge transfer in tissue, comprising a coil generating a changing magnetic field to induct an electric field in the tissue exceeding 10 mV/cm when said coil is 5 cm from the tissue, said coil having a duty cycle of at least ten percent.

12. The apparatus according to claim 11, wherein said coil has a duty cycle of at least eighty percent.

13. A method for magnetically inducting an electrical field in tissue to create therapeutic charge transfer in the tissue, which comprises:
    providing an apparatus for creating therapeutic charge transfer in tissue, comprising a coil generating a changing magnetic field to induct an electric field in the tissue exceeding 10 mV/cm when said coil is 5 cm from the tissue;
    increasing the magnetic field in said coil linearly over time to induct an electrical field having a first direction in the tissue for a first period of time; and
    decreasing the magnetic field linearly over time to induct an electrical field having a second direction opposite said first direction in the tissue for a second period time, the second period of time being different than said first period of time.

14. The method according to claim 13, wherein the first period of time is longer time than the second period of time.

15. The method according to claim 14, which further comprises minimizing said second period of time.

16. The method according to claim 13, which further comprises repeating the increasing step and the decreasing step.

17. The method according to claim 13, wherein the increasing and the decreasing of said magnetic field has a saw-tooth shaped intensity over time.

18. The method according to claim 13, wherein said first period of time is at least five times as long as said second period of time.

19. The method according to claim 13, wherein the increasing of said magnetic field includes increasing said magnetic field at a sufficient rate so that said electric field in the tissue is at least 10 mV/cm.

20. The method according to claim 13, which further comprises:
creating an ionic charge transfer in the tissue in a first direction during the increasing step; and
creating an ionic charge transfer in the tissue in a second direction opposite said first direction during the decreasing step; and
controlling a rate of change of said magnetic field and duration of the increasing step and the decreasing step so that said charge transfer in said second direction is no more than half said charge transfer in said first direction.

21. A method for magnetically inducting an electrical field in tissue to create therapeutic charge transfer in the tissue, which comprises:
providing an apparatus for creating therapeutic charge transfer in tissue, comprising a coil generating a changing magnetic field to induct an electric field in the tissue exceeding 10 mV/cm when said coil is 5 cm from the tissue;
increasing the magnetic field in said coil steadily to induct an electrical field having a first direction in the tissue for a first period of time varying less than 10% in intensity for at least 90% of said first period of time; and
decreasing the magnetic field to induct an electrical field having a second direction opposite said first direction in the tissue for a second period time, the second period of time being different than said first period of time.

22. A method for magnetically inducting an electrical field in tissue to create therapeutic charge transfer in the tissue, which comprises:
providing an apparatus for creating therapeutic charge transfer in tissue, comprising a coil generating a changing magnetic field to induct an electric field in the tissue exceeding 10 mV/cm when said coil is 5 cm from the tissue;
increasing the magnetic field in said coil to induct an electrical field having a first direction in the tissue for a first period of time;
decreasing the magnetic field to induct an electrical field having a second direction opposite said first direction in the tissue for a second period time, the second period of time being different than said first period of time;
repeating the increasing and the decreasing steps in alternating order;
defining a duty cycle as said first time period divided by a sum of said first and second time period; and
maintaining said duty cycle to at least sixty-three percent.

23. A method for magnetically inducting an electrical field in tissue to create therapeutic charge transfer in the tissue, which comprises:
providing an apparatus for creating therapeutic charge transfer in tissue, comprising a coil generating a changing magnetic field to induct an electric field in the tissue exceeding 10 mV/cm when said coil is 5 cm from the tissue;
increasing the magnetic field in said coil to induct an electrical field having a first direction in the tissue for a first period of time; and
decreasing the magnetic field to induct an electrical field having a second direction opposite said first direction in the tissue for a second period time, the second period of time being different than said first period of time;
creating said magnetic field in a coil;
connecting said coil to an increase subcircuit that feeds current to said coil during the increasing step; and
connecting said coil to a decrease subcircuit that robs current from said coil during the decreasing step.

24. The method according to claim 23, which further comprises:
interconnecting said coil and said increase subcircuit with an Integrated Gate Bipolar Transistor (IGBT); and
interconnecting said coil and said decrease subcircuit with said IGBT.

25. The method according to claim 24, wherein said IGBT has a stand-off voltage of at least two thousand volts.

26. The method according to claim 23, which further comprises:
passing an electrical current through said coil to create said magnetic field; and
during the increasing step, raising said electrical current to at least one thousand watts.

* * * * *